United States Patent
Coe et al.

(10) Patent No.: US 8,428,747 B2
(45) Date of Patent: *Apr. 23, 2013

(54) LEAD LOCKING DEVICE AND METHOD

(75) Inventors: Michael Sean Coe, Colorado Springs, CO (US); Kenneth D. Harlan, Peyton, CO (US); Cesar Diaz, Santa Margarita, CA (US); Thomas E. Plasket, Colorado Springs, CO (US)

(73) Assignee: The Spectranetics Corp., Colorado Springs, CO (US)

( * ) Notice: Subject to any disclaimer, the term of this patent is extended or adjusted under 35 U.S.C. 154(b) by 1493 days.

This patent is subject to a terminal disclaimer.

(21) Appl. No.: 10/877,190

(22) Filed: Jun. 25, 2004

(65) Prior Publication Data

US 2004/0236397 A1 Nov. 25, 2004

Related U.S. Application Data

(60) Division of application No. 09/931,961, filed on Aug. 20, 2001, now Pat. No. 6,772,014, which is a continuation-in-part of application No. 09/727,509, filed on Dec. 4, 2000, now Pat. No. 6,324,434, which is a division of application No. 09/285,720, filed on Apr. 5, 1999, now Pat. No. 6,167,315.

(51) Int. Cl.
*A61N 1/00* (2006.01)
(52) U.S. Cl.
USPC ........................................................ 607/116
(58) Field of Classification Search .................. 604/264; 606/108; 607/115, 119, 126, 116
See application file for complete search history.

(56) References Cited

U.S. PATENT DOCUMENTS

| 3,789,841 A | 2/1974 | Antoshkiw |
| 3,871,382 A | 3/1975 | Mann |
| 3,906,938 A | 9/1975 | Fleischhacker |
| 4,000,745 A | 1/1977 | Goldberg |
| 4,471,777 A | 9/1984 | McCorkie, Jr. |
| 4,498,482 A | 2/1985 | Williams |
| 4,541,681 A | 9/1985 | Dorman et al. |
| 4,545,390 A | 10/1985 | Leary |
| 4,574,800 A | 3/1986 | Peers-Trevarton |

(Continued)

OTHER PUBLICATIONS

European Search Report for European Patent Application No. 00106944.2, dated Jan. 2, 2001, 3 pages.

(Continued)

*Primary Examiner* — Scott M Getzow
(74) *Attorney, Agent, or Firm* — Sheridan Ross P.C.

(57) ABSTRACT

A lead locking device has a lead insertion member having a proximal end and a distal end and has a lead engaging assembly. The lead insertion member defines a lumen extending along a longitudinal axis between the distal end and the proximal end of the lead engaging assembly. A mandrel disposed in the lumen of the lead engaging assembly extends along substantially the entire length of the lumen and protrudes beyond the most proximal end of the lead insertion member. The mandrel includes a distal portion in slidable contact with at least a portion of the lead engaging assembly. The lead engaging assembly has a first configuration while being inserted into a lumen of a lead and a second configuration while engaging the lead from within the lumen of the lead. The lead engaging member has at least two expansion jaws that, in the first configuration, define a substantially cylindrical body. The expansion jaws translate radially outwardly from the longitudinal axis to engage the lumen of the lead when in the second configuration.

13 Claims, 16 Drawing Sheets

U.S. PATENT DOCUMENTS

| | | | |
|---|---|---|---|
| 4,576,162 A | 3/1986 | McCorkie | |
| 4,582,056 A | 4/1986 | McCorkie et al. | |
| 4,706,671 A | 11/1987 | Weinrib | |
| 4,721,118 A | 1/1988 | Harris | |
| 4,762,130 A | 8/1988 | Fogarty et al. | |
| 4,791,939 A | 12/1988 | Maillard | |
| 4,796,642 A | 1/1989 | Harris | |
| 4,827,941 A | 5/1989 | Taylor et al. | |
| 4,943,289 A | 7/1990 | Goode et al. | |
| 4,988,347 A | 1/1991 | Goode et al. | |
| 5,011,482 A | 4/1991 | Goode et al. | |
| 5,013,310 A | 5/1991 | Goode et al. | |
| 5,207,683 A | 5/1993 | Goode et al. | |
| 5,231,996 A | 8/1993 | Bardy et al. | |
| 5,313,967 A | 5/1994 | Leiber et al. | |
| 5,360,441 A * | 11/1994 | Otten | 607/122 |
| 5,365,944 A | 11/1994 | Gambale | |
| 5,423,806 A | 6/1995 | Dale et al. | |
| 5,423,876 A | 6/1995 | Camps et al. | |
| 5,514,128 A * | 5/1996 | Hillsman et al. | 606/7 |
| 5,549,615 A | 8/1996 | Hocherl et al. | |
| 5,556,424 A * | 9/1996 | Hocherl et al. | 607/116 |
| 5,593,433 A | 1/1997 | Spehr et al. | |
| 5,620,451 A | 4/1997 | Rosborough | |
| 5,628,773 A | 5/1997 | Jasch | |
| 5,632,749 A | 5/1997 | Goode et al. | |
| 5,674,217 A * | 10/1997 | Wahlstrom et al. | 606/15 |
| 5,697,936 A | 12/1997 | Shipko et al. | |
| 5,755,765 A * | 5/1998 | Hyde et al. | 607/122 |
| 5,769,858 A * | 6/1998 | Pearson et al. | 606/108 |
| 5,865,843 A | 2/1999 | Baudino | |
| 5,871,531 A | 2/1999 | Struble | |
| 5,919,224 A | 7/1999 | Thompson et al. | |
| 6,136,005 A | 10/2000 | Goode et al. | |
| 6,167,315 A | 12/2000 | Coe et al. | |
| 6,185,464 B1 * | 2/2001 | Bonner et al. | 607/119 |
| 6,324,434 B2 | 11/2001 | Coe et al. | |
| 6,356,791 B1 * | 3/2002 | Westlund et al. | 607/115 |
| 6,419,674 B1 * | 7/2002 | Bowser et al. | 606/45 |
| 6,527,732 B1 | 3/2003 | Strauss et al. | |
| 6,772,014 B2 | 8/2004 | Coe et al. | |
| 7,499,756 B2 | 3/2009 | Bowe et al. | |
| 2002/0147487 A1 | 10/2002 | Sundquist et al. | |
| 2003/0074040 A1 | 4/2003 | Florio et al. | |
| 2004/0236396 A1 | 11/2004 | Coe et al. | |
| 2004/0236397 A1 | 11/2004 | Coe et al. | |
| 2005/0027343 A1 | 2/2005 | Westlund et al. | |
| 2005/0137674 A1 * | 6/2005 | Coe et al. | 607/130 |

OTHER PUBLICATIONS

Extended European Search Report for European Patent Application No. 06735255.9, dated May 8, 2009, 7 pages.

International Preliminary Report on Patentability for PCT/US2006/005501 mailed Sep. 11, 2007 including Written Opinion of the International Searching Authority mailed Aug. 17, 2007, 5pgs.

International Search report for PCT/US 06/05501 mailed Aug. 17, 2007, 1pg.

* cited by examiner

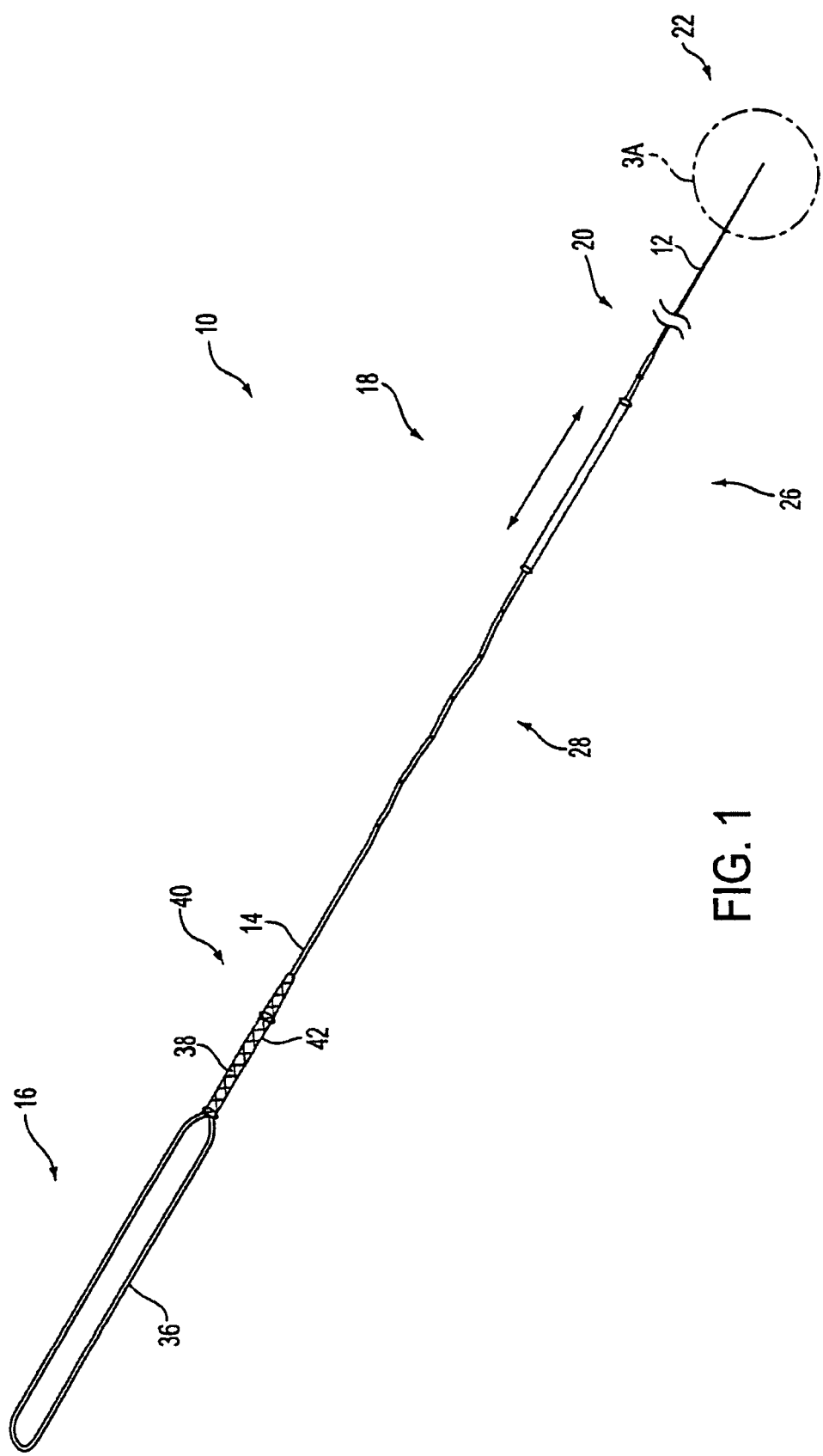

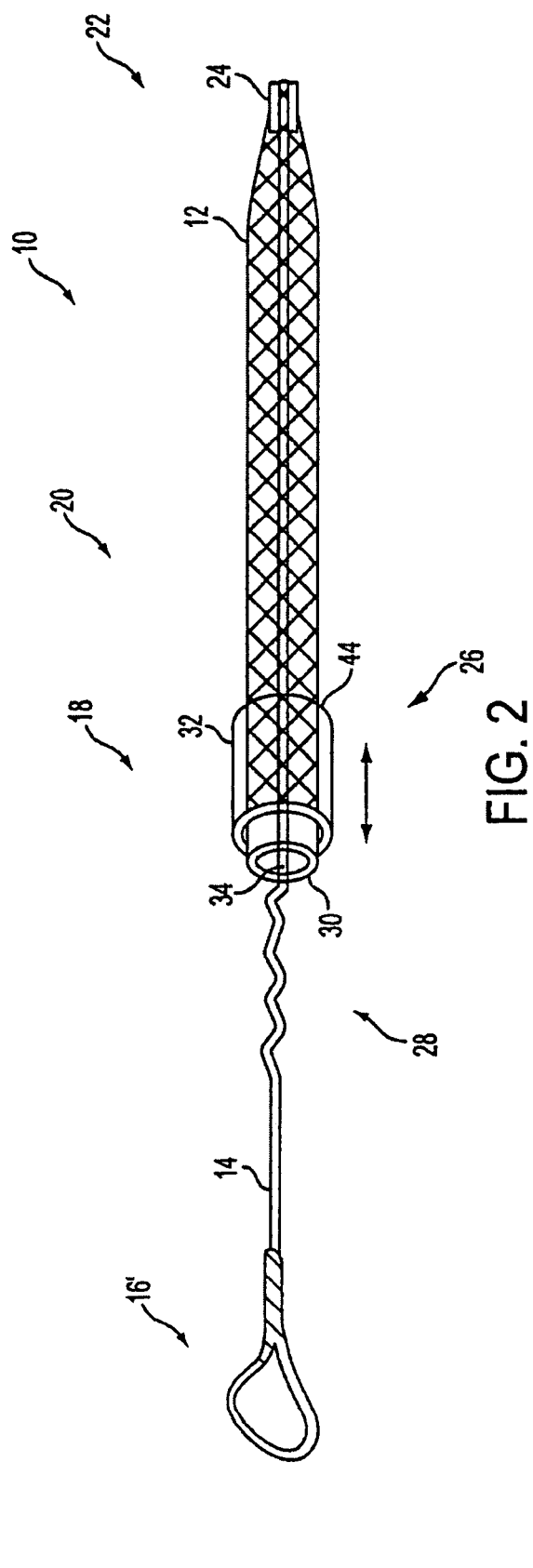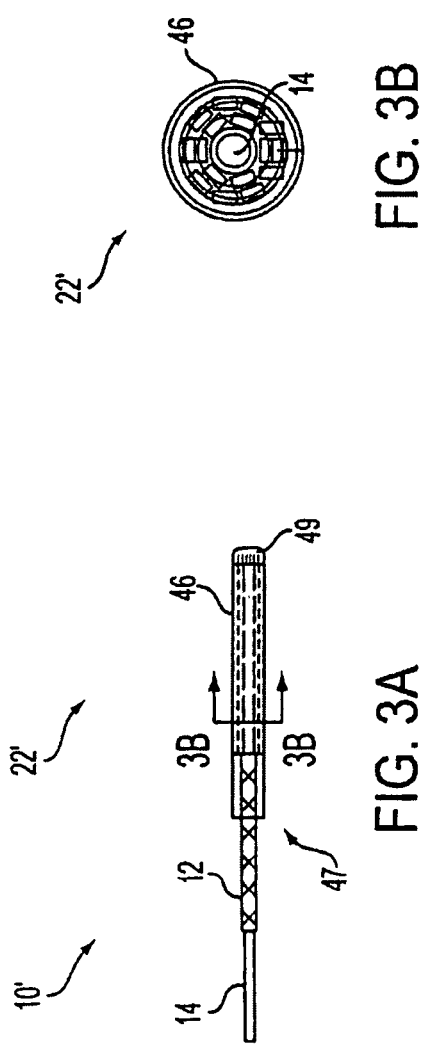

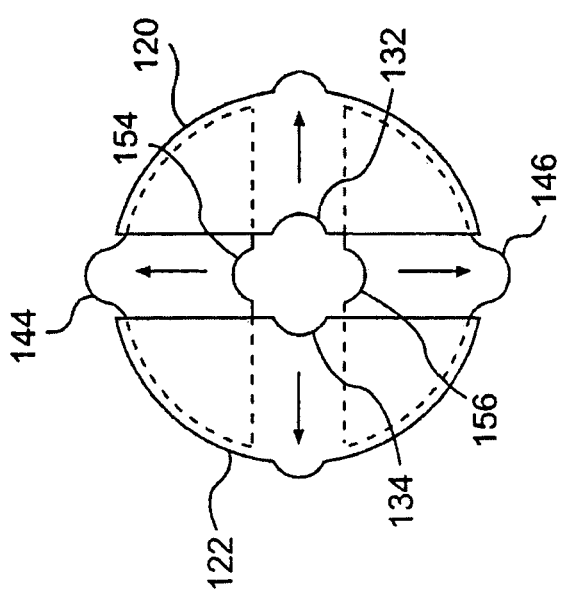
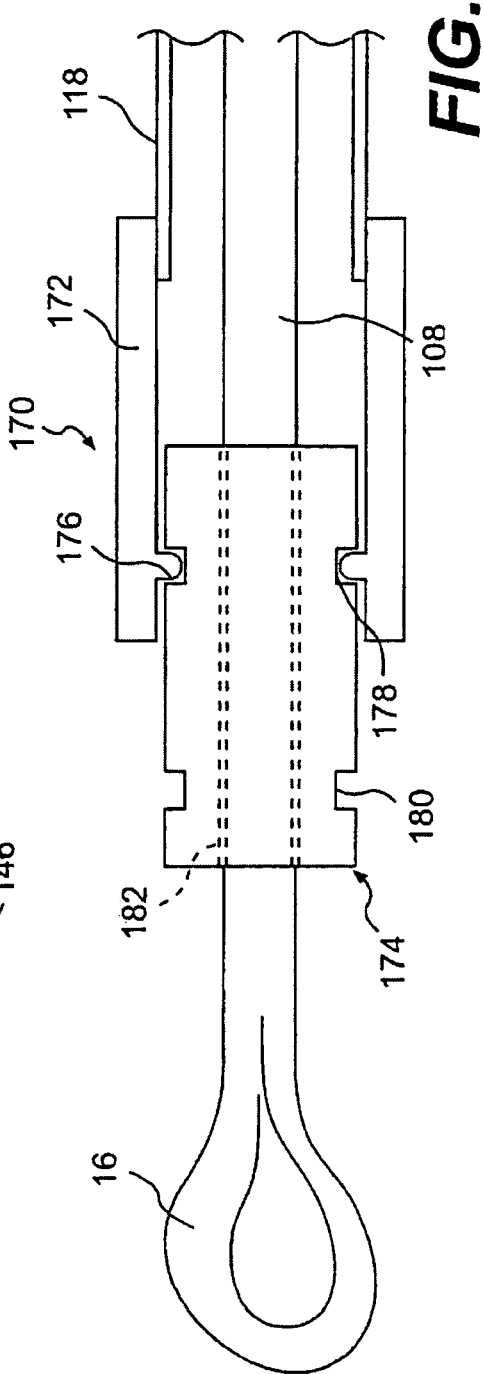

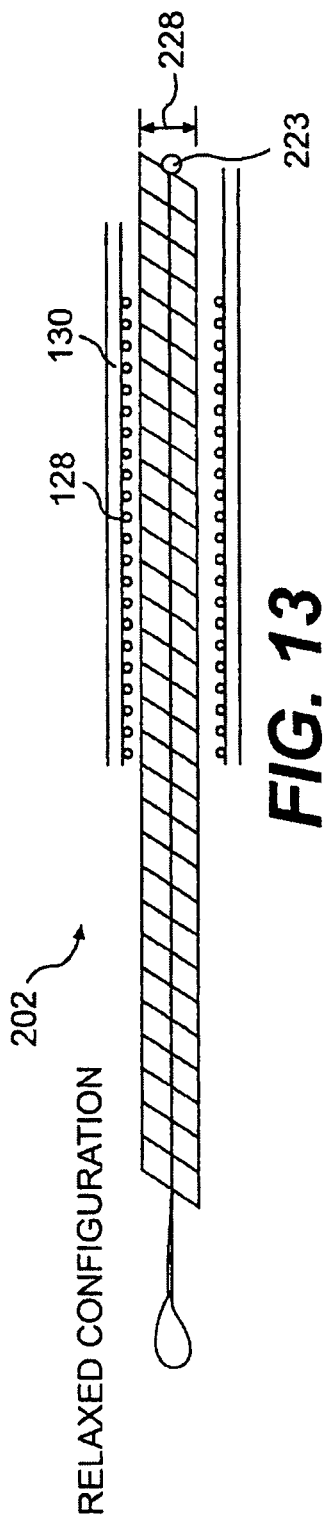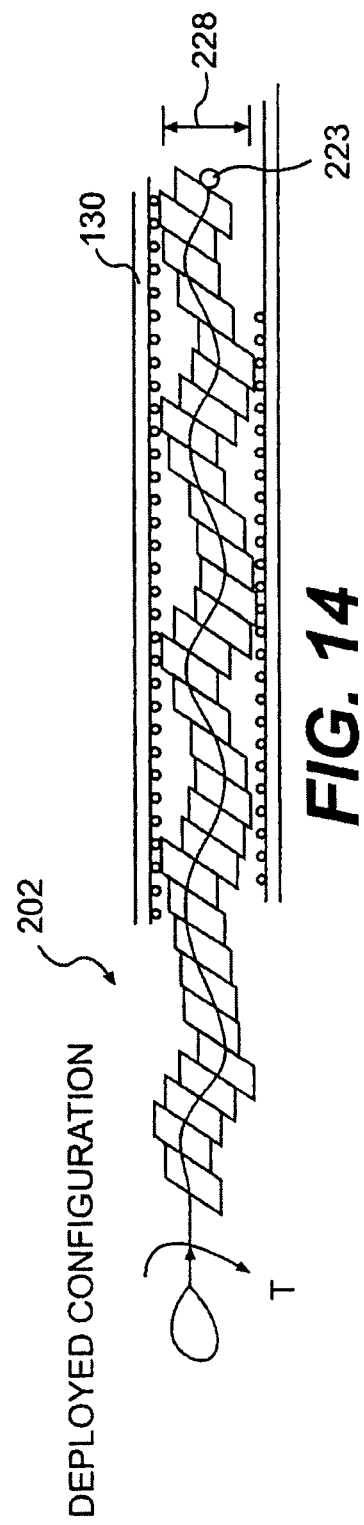

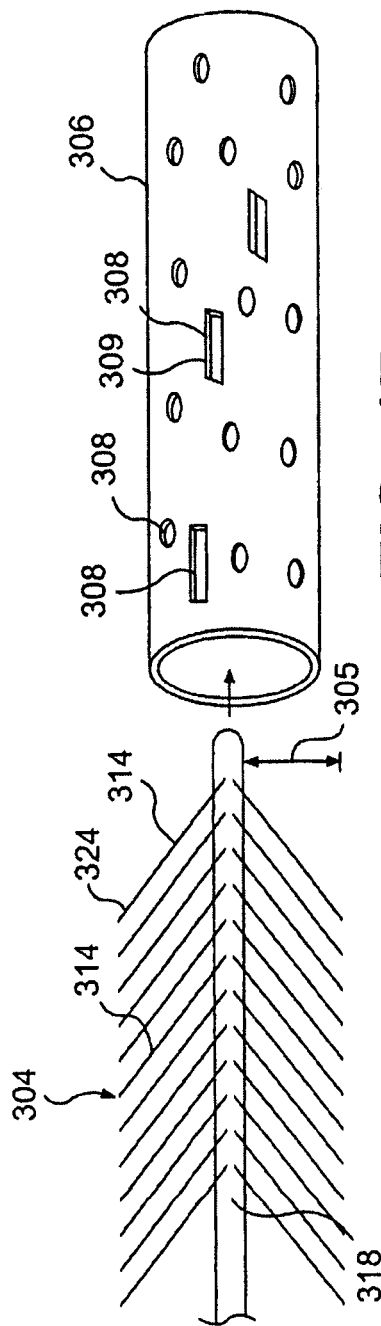
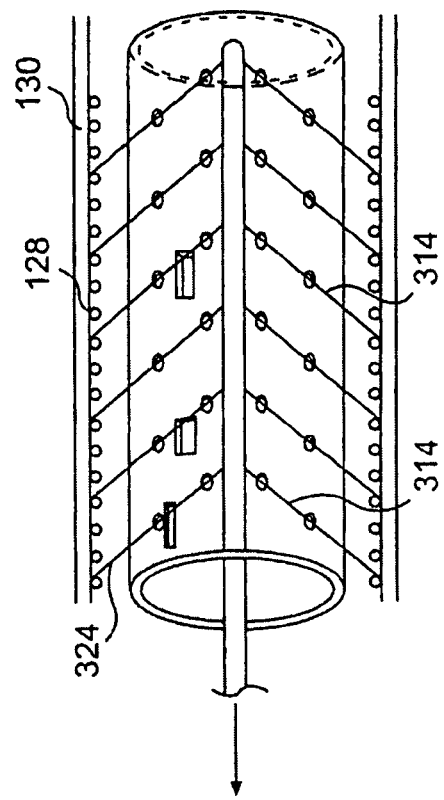
FIG. 17
FIG. 18
FIG. 19

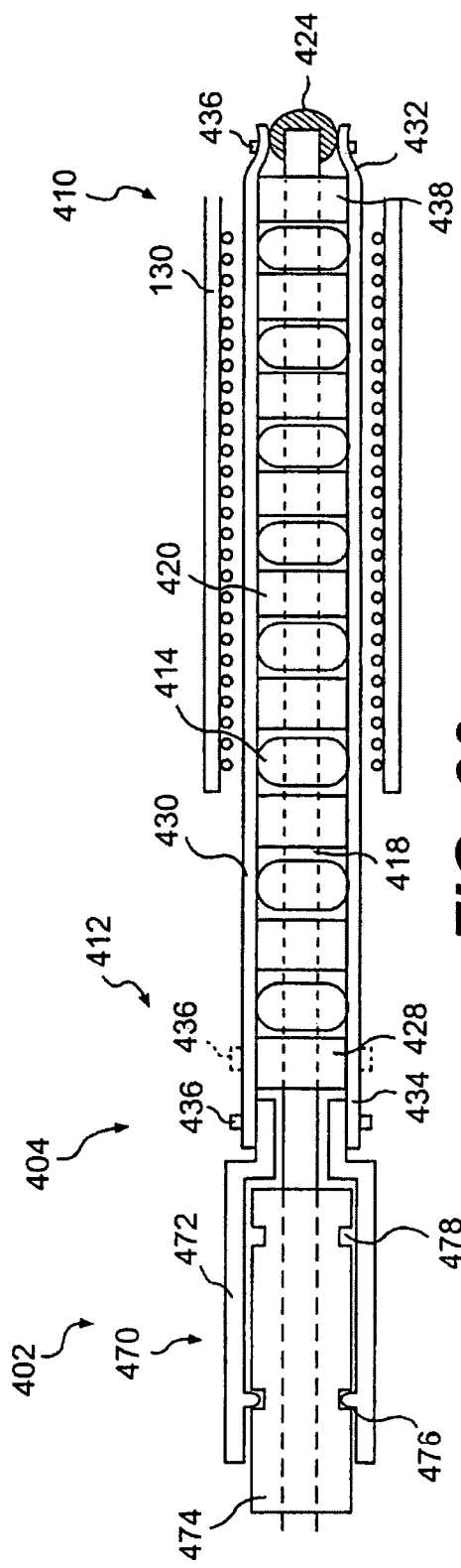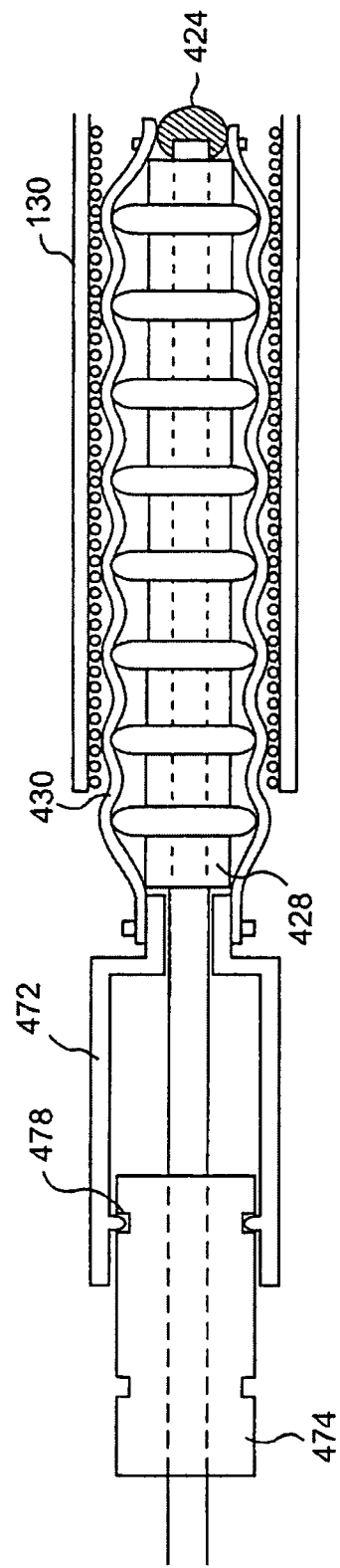

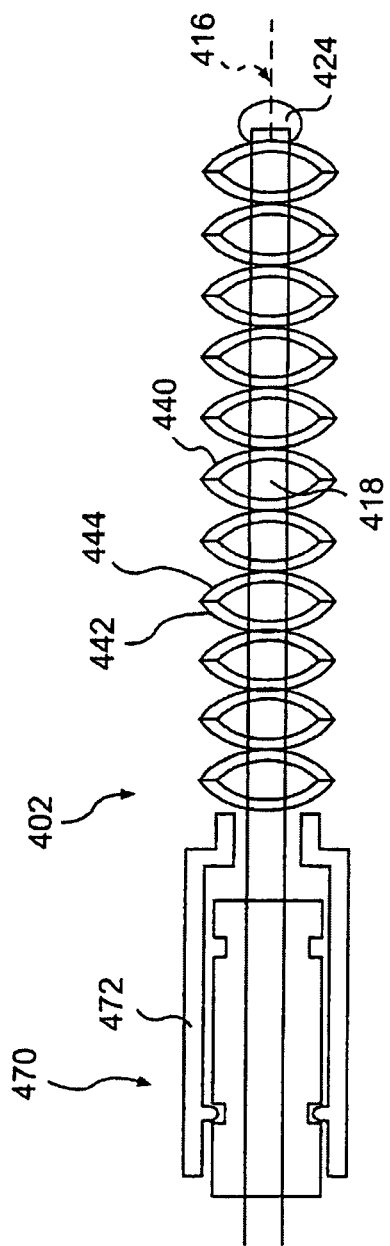
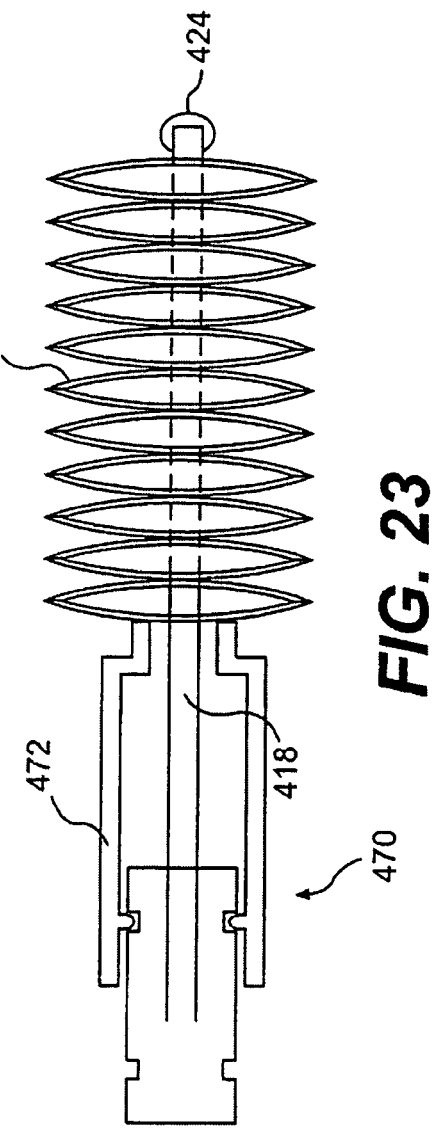
FIG. 22
FIG. 23

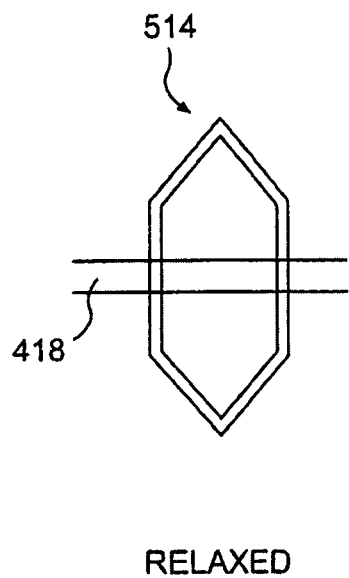
RELAXED
FIG. 26
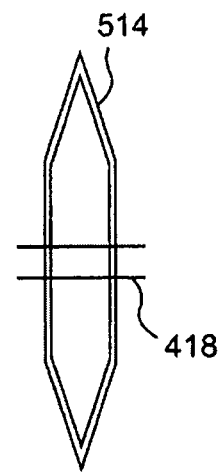
DEPLOYED
FIG. 27
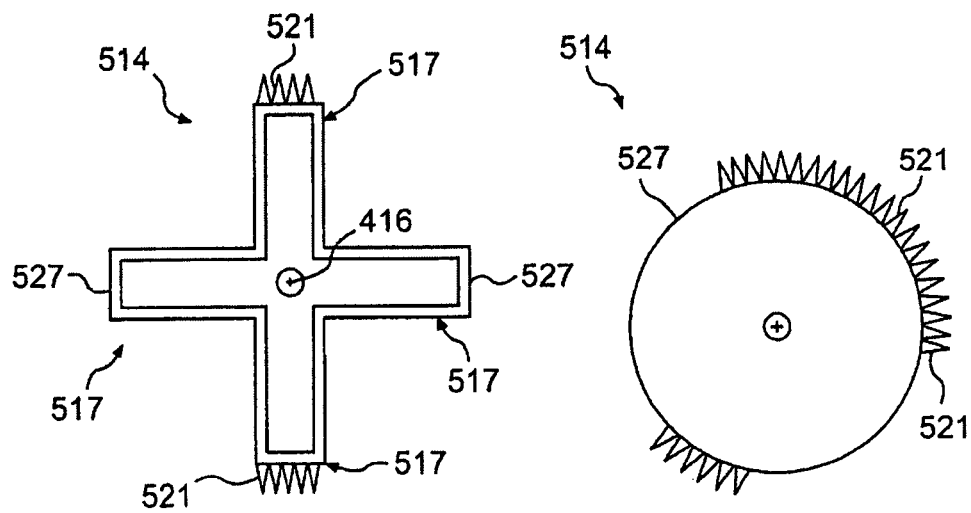
FIG. 28
FIG. 29

LEAD LOCKING DEVICE AND METHOD

This application is a divisional application of and claims the benefit of continuation-in-part U.S. application Ser. No. 09/931,961, filed Aug. 20, 2001, and of U.S. application Ser. No. 09/727,509, filed on Dec. 4, 2000, and of U.S. application Ser. No. 09/285,720, which issued as U.S. Pat. No. 6,167,315 on Dec. 26, 2000, the 09/727,509 application being a Divisional Application of the 09/285,720 application, the entire contents of each application being hereby incorporated into the present application by reference.

BACKGROUND OF THE INVENTION

1. Field of the Invention

This invention pertains to lead locking devices and methods for locking onto a lead, and more particularly to lead locking devices and methods for locking onto and removing a lead, such as a pacemaker lead, from a patient's body.

2. Description of Related Art

Various medical procedures attach wire-like devices to internal portions of a person's body, such as an electrical lead for a pacemaker or a catheter. Pacemaker leads are electrically conducting wires which run to an electrode that is attached to an inner wall of a person's heart. Pacemaker leads are typically a coil of wire enclosed in an outer cylindrical sheath of electrically insulating material. The coil of wire usually leaves a hollow space running down the center of the pacing lead (a "lumen").

Pacing leads are usually implanted with the intention that they will remain in the patient for several years. During such time, fibrous tissue grows over the electrode and portions of the lead. Pacing leads are often provided with additional barb-like structures or a corkscrew type of structure to encourage adhesion to the inner wall of the patient's heart.

Pacing leads sometimes fail or it is sometimes desirable to place an electrode at a different position from a previous position. It is then necessary to determine what should be done with the unused pacing leads. Both the removal of a pacing lead and leaving it in the patient entail associated risks. Leaving the pacing lead in the patient can increase the chances of infection, interfere with the additional pacing leads, or cause additional complications. On the other hand, removing pacing leads can cause severe, and possibly fatal, damage to the patient's heart.

Numerous devices have thus been developed that can be inserted into the lumen of a pacing lead to be attached to the pacing lead close to the electrode in order to apply traction to the end of the lead that is close to the electrode. A series of patents to Goode et al (U.S. Pat. Nos. 4,943,289; 4,988,347; 5,011,482; 5,013,310; and 5,207,683) disclose various devices which attach to the pacing lead at a localized region close to the electrode. Peers-Trevarton (U.S. Pat. No. 4,574,800), Hocherl et al (U.S. Pat. No. 5,549,615) and McCorkle (U.S. Pat. Nos. 4,471,777 and 4,582,056) disclose similar devices which attach to a pacing lead close to the electrode. However, all of these devices have a disadvantage that they attach to the pacing lead in a localized area. Applying traction to the pacing lead and/or pacing lead removing devices according to the prior art can result in the pacing lead becoming distorted and/or breaking before it can be removed from the patient. In addition, the prior art devices rely on either a form of entanglement with the coiled wire of the pacing lead, or some form of local distortion to the coil of the pacing lead in order to maintain a firm grip with the pacing lead removing apparatus while traction is applied to the apparatus. Consequently, this makes it difficult or impossible to remove a conventional device from the pacing lead in order to abort or restart the pacing lead removing procedure.

The expandable portions of the conventional devices also make it difficult or impossible to use other lead removing equipment and procedures in conjunction with those devices. For example, a substantially cylindrical and flexible catheter which has a central lumen is often slid over the pacing lead such that the pacing lead passes through the lumen of the catheter and the leading edge of the catheter is used to free fibrous growth from the pacing lead. Laser catheters are also known to slide over a pacing lead in which laser light is transmitted along the catheter in order to cut away fibrous tissue as the laser catheter is advanced along the pacing lead. It is also known to use a pair of telescoping catheters, both of which slide over the pacing lead. Consequently, it is also desirable to have a pacing lead removing device which can attach internally to the pacing lead so as not to obstruct a catheter or laser catheter which may be used in conjunction with the pacing lead removing device.

SUMMARY OF THE INVENTION

Accordingly, it is an object of this invention to provide a lead locking device which is insertable into a lumen of a lead and which engages and forms a grip with an extended portion of the inner region of the lead.

It is another object of this invention to provide a lead locking device which is insertable into a lumen of a lead and which engages and forms a grip with an extended portion of the inner region of the lead including at least a proximal portion.

It is another object of this invention to provide a lead locking device which is insertable into a lumen of a lead and engages the lead substantially along the entire length of the lead to form a grip with the lead.

It is another object of this invention to provide a lead locking device and catheter combination for removing a lead, such as a pacemaker lead, from a patient's body.

It is another object of this invention to provide a method of removing a pacing lead by attaching a lead locking device to an extended portion of a lead within the lumen of the lead.

It is another object of this invention to provide a method of removing a lead from a patient's body by attaching a lead locking device along substantially the entire length of a lead.

The above and related objects of this invention are realized by providing a lead locking device that has a lead insertion member having a proximal end and a distal end. The lead insertion member has a lead engaging assembly that defines a lumen extending along a longitudinal axis between the distal end and the proximal end of the lead engaging assembly, a mandrel disposed in the lumen of the lead engaging assembly extending along substantially the entire length of the lumen and protruding beyond the most proximal end of the lead insertion member. The mandrel includes a distal portion in slidable contact with at least a portion of the lead engaging assembly. The lead engaging assembly has a first configuration while being inserted into a lumen of a lead and a second configuration while engaging the lead from within the lumen of the lead. The lead engaging member has at least two expansion jaws that, in the first configuration, define a substantially cylindrical body. The at least two expansion jaws translate radially outwardly from the longitudinal axis to engage the lumen of the lead when in the second configuration.

In another embodiment of the invention, a lead locking device has a lead engaging member having a distal end and a proximal end. The lead engaging member includes a series of juxtaposed sections, each section forming a through hole and each through hole being aligned with an adjacent through hole of an adjacent section to define a bore hole extending along a longitudinal axis between the distal end and the proximal end; a mandrel disposed in the bore hole and fixedly attached to at least one of the sections of the lead engaging member, the mandrel extending along substantially the entire length of the bore hole and protruding beyond the most proximal end of the lead engaging member. The lead engaging member has a first configuration while being inserted into a lumen of a lead and a second configuration while engaging the lead from within the lumen of the lead.

In another embodiment of the invention, a method of removing a lead implanted in a patient's body includes inserting a lead locking device into a lumen defined by the lead, the lead locking device comprising a lead engaging member that extends along substantially the entire length of the lead, the lead engaging member having a narrower overall radial dimension in a relaxed configuration than in a radially torqued configuration. The lead engaging member is in the relaxed configuration during the insertion of the lead locking device. The method also includes applying a torque to the lead engaging member, wherein applying the torque to the lead engaging member causing the lead engaging member to have an overall radial dimension that is substantially equal to an inner diameter of the lumen of the lead. The method also includes applying traction to the lead locking device. The lead engaging member engages the lead along substantially the entire longitudinal length of the lead.

In another embodiment of the invention, a lead locking device has a hypotube defining a plurality of openings therein, the hyptotube having a longitudinal axis extending between a distal end and a proximal end thereof; and a lead engaging member disposed in the hypotube, the lead engaging member including a plurality of bristles radially extending from a mandrel, the bristles being resiliently biased in an outward radial direction of the longitudinal axis, the mandrel being disposed generally along the longitudinal axis and extending along substantially the entire length of the hypotube and protruding beyond the most proximal end of the hypotube. The lead engaging member has a first configuration while being inserted into a lumen of a lead and a second configuration while engaging the lead from within the lumen of the lead.

In another embodiment of the invention, a method of removing a lead implanted in a patient's body includes inserting a lead locking device into a lumen defined by the lead, the lead locking device having a hypotube that has a plurality of openings formed therein, and a lead engaging member disposed in the hypotube. The lead engaging member includes a plurality of bristles radially extending from a mandrel, the bristles being resiliently biased in the outward radial direction of the longitudinal axis, and disposed within the hypotube in a first configuration for inserting the lead locking device into the lead. The method also includes applying an axial force to the mandrel so that bristles of the lead engaging member protrude from the openings to engage the lead. The overall radial dimension of the distal ends of the bristles is substantially equal to an inner diameter of the lumen of the lead. The method further includes applying traction to the lead locking device. The lead engaging member engages the lead along substantially the entire longitudinal length of the lead.

In another embodiment of the invention, a lead locking device has a mandrel and a lead engaging member that has a distal end and a proximal end. The lead engaging member includes a plurality of radially expandable elastic members disposed around the mandrel. The mandrel extends along a longitudinal axis between the distal end and the proximal end, the mandrel protruding beyond the most proximal end of the lead engaging member. The lead engaging member has a first configuration while being inserted into a lumen of a lead and a second configuration while engaging the lead from within the lumen of the lead.

In another embodiment of the invention, a method of removing a lead implanted in a patient's body includes inserting a lead locking device into a lumen defined by the lead. The lead locking device has a plurality of radially expandable elastic members disposed around a mandrel, each of the plurality of radially expandable elastic members having a smaller radial dimension in a relaxed configuration than in a compressed configuration, wherein the elastic members are in a relaxed configuration during the insertion of the lead locking device. The method also includes applying an axial compressive force to the elastic members so that the elastic members of the lead engaging member extend radially outwardly to engage the lumen of the lead in the compressed configuration, wherein the transverse diameter of some of the elastic members in the compressed configuration are substantially equal to an inner diameter of the lumen of the lead. The method further includes applying traction to the lead locking device. The lead engaging member engages the lead along substantially the entire longitudinal length of the lead.

BRIEF DESCRIPTION OF THE DRAWINGS

These and other objects and advantages of the invention will become more apparent and more readily appreciated from the following detailed description of the presently preferred exemplary embodiments of the invention, taken in conjunction with the accompanying drawings, of which:

FIG. 1 illustrates a lead locking device according to a first embodiment of the invention;

FIG. 2 is a schematic illustration of the lead locking device according to the first embodiment of the invention;

FIG. 3A is a blown-up view of a section of FIG. 1;

FIG. 3B is a cross-sectional view of the portion of the lead locking device illustrated in FIG. 3A;

FIG. 10 illustrates a front view of the first lead engaging member of the fifth embodiment;

FIG. 11 is a blown-up view of a section of FIG. 8;

FIG. 13 illustrates the sixth embodiment of a lead locking device in a relaxed configuration;

FIG. 14 illustrates the sixth embodiment of a lead locking device in a deployed configuration;

FIG. 17 is a blown-up view of a section of FIG. 16 in an unassembled configuration;

FIG. 18 is a blown-up view of a section of FIG. 16 in the relaxed configuration;

FIG. 19 is a blown-up view of a section of FIG. 16 in the deployed configuration;

FIG. 20 illustrates an eighth embodiment of a lead locking device in a relaxed configuration (first configuration);

FIG. 21 illustrates the eighth embodiment of a lead locking device in a deployed configuration (second configuration);

FIG. 22 illustrates a variation of the eighth embodiment in a relaxed configuration;

FIG. 23 illustrates the lead locking device illustrated in FIG. 22 in a deployed configuration (second configuration);

FIG. 26 illustrates a variation of the ninth embodiment;

FIG. 27 illustrates the variation of FIG. 26 in the deployed configuration (second configuration);

FIG. 28 illustrates a variation of the ninth embodiment; and

FIG. 29 illustrates a variation of the ninth embodiment.

DETAILED DESCRIPTION

Figure 4:
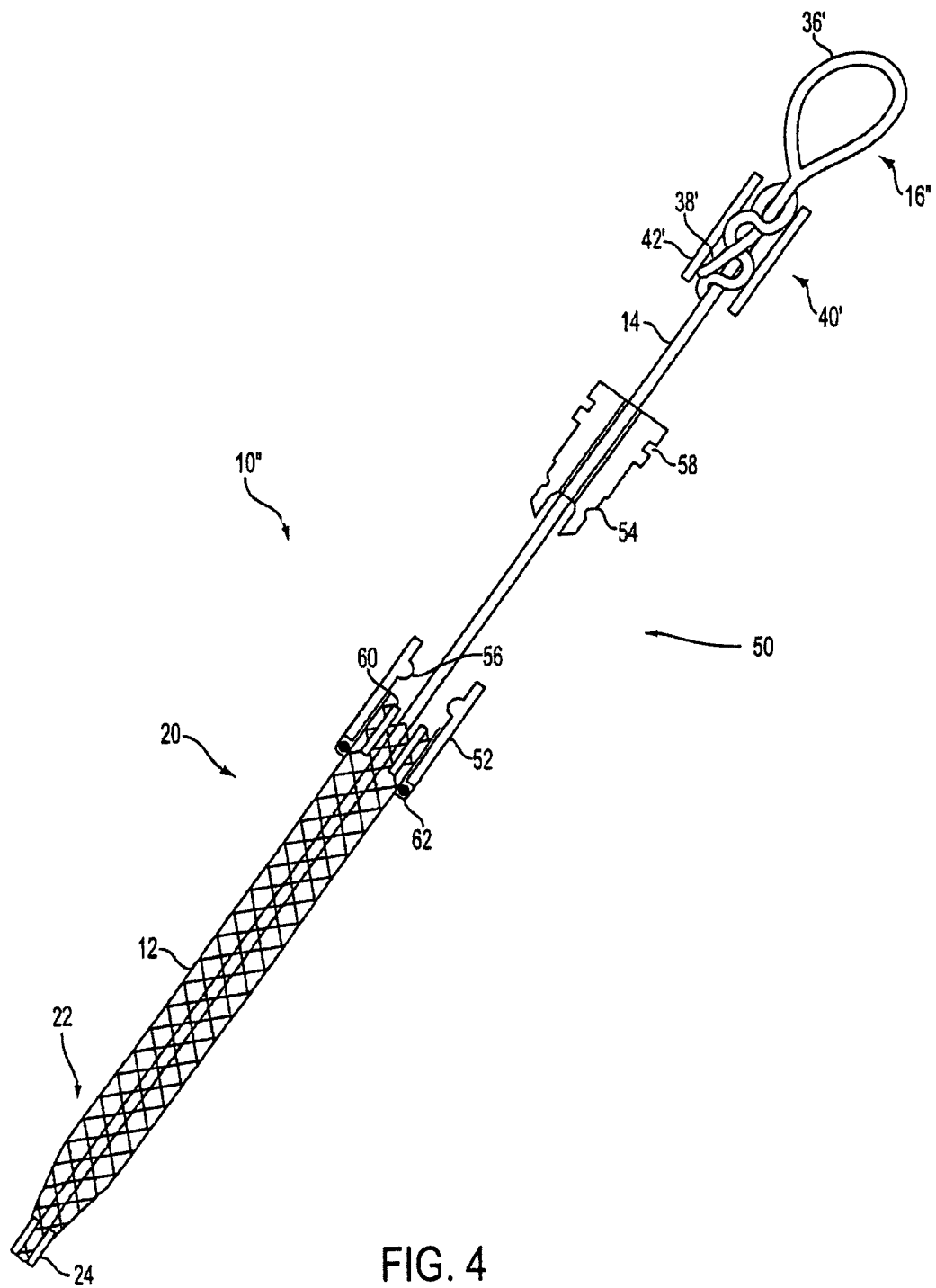
FIG. 4 is a schematic illustration of a lead locking device which has a second embodiment of a mechanism to hold the lead engaging member in a stretched configuration.

Reference numeral 10 in FIG. 1 generally represents a lead locking device according to a first embodiment of the invention. The lead locking device 10 has a lead engaging member 12, a mandrel 14, a loop handle 16 and a press-fit type of latching mechanism 18. The lead engaging member 12 has a proximal end 20 and a distal end 22. FIG. 1 shows a section of the lead engaging member 12, between the proximal end 20 and the distal end 22, with the center portion cut away for illustration purposes. Consequently, FIG. 1 does not illustrate the scaled length of the lead engaging member 12. Preferably, the lead engaging member 12 is at least about 65 cm long. However, the length of the lead engaging member 12 may be selected according to the intended application. As one may see illustrated schematically in FIG. 2, the lead engaging member 12 defines a lumen extending between the proximal end 20 and distal end 22. The mandrel 14 is disposed in the lumen defined by the lead engaging member 12 and attached to the distal tip 24 of the lead engaging member 12. In a preferred embodiment, the lead engaging member 12 is a braided sheath. The lead engaging member 12 is soldered to the mandrel 14 at the distal tip 24 in a first embodiment. The solder at the distal tip 24 is preferably a radiopaque solder. Suitable materials for the radiopaque solder are alloys of gold and tin. More preferably, the solder at the distal tip 24 is about 80% gold and about 20% tin.

In a preferred embodiment, the press-fit type of latching mechanism 18 has at least a portion 26 attached to the proximal end 20 of the lead engaging member 12 and a crimped portion 28 of the mandrel 14. Preferably, the portion of the press-fit mechanism 26 attached to the proximal end 20 of the lead engaging member 12 has an inner hypotube 30 and an outer hypotube 32 concentrically arranged to sandwich the proximal end 20 of the lead engaging member 12 therebetween. Preferably, the inner hypotube 30 and outer hypotube 32 are crimped to become mechanically fixed to the lead engaging member 12. The inner hypotube 30 and outer hypotube 32, which are preferably rigidly fixed with respect to each other and to a proximal end 20 of the lead engaging member 12, is slidable along the mandrel 14 disposed in the lumen defined by the lead engaging member 12. The crimped section 28 in the mandrel 14 is constructed at a position relative to the proximal end 20 of the lead engaging member 12 such that the inner hypotube 30 and outer hypotube 32 attached to the proximal end 20 of the lead engaging member 12 overlaps the crimped section 28 of the mandrel 14 when the lead engaging member 12 is in a stretched configuration. More preferably, the inner hypotube 30 and outer hypotube 32 attached to the proximal end 20 of the lead engaging member 12 sets in a stable condition, thus being held or "latched" in place, approximately in the center of the crimped section 28 when the lead engaging member 12 is in a stretched configuration. In the preferred embodiment, the inner hypotube 30 and outer hypotube 32 attached to the proximal end 20 of the lead engaging member 12 is beyond the most distal end 34 in the distal direction when the lead engaging member 12 is in a substantially relaxed configuration.

As one may see illustrated in FIG. 1, the loop handle 16 of the lead locking device 10 preferably has a proximal loop 36 and an end portion 38 which is further twisted around the most proximal end 40 of the mandrel 14. In the preferred embodiment, a proximal loop hypotube 42 is disposed over the twisted end 38 of the loop handle 16 and crimped to mechanically attach the loop handle 16 to the mandrel 14. Preferably, the proximal loop hypotube-42 is crimped, thereby forming a solid mechanical attachment of the loop handle 16 to the mandrel 14.

Preferably, the proximal loop 36 is made from annealed stainless steel wire, thus providing a degree of malleability. More preferably, the stainless steel wire of the proximal loop 36 is an annealed portion of the most proximal end of the mandrel 14 itself. Stainless steel 304V wire about 0.020" thick with about 20 cm annealed at the proximal end has been found to be suitable for the mandrel 14 with a proximal loop 36. Preferably, the proximal loop hypotube 42 is 304V stainless steel.

In the preferred embodiment, the mandrel 14, the inner hypotube 30 and the outer hypotube 32 are 304V stainless steel. In the first preferred embodiment, the lead engaging member 12 is a braided sheath. Preferably, the lead engaging member 12 is a braided sheath of flat wires which have a rectangular cross-section. Preferably, the flat wires of the braided sheath of the lead engaging member 12 are 304V stainless steel. More preferably, the flat wires have cross-sectional dimensions of about 0.001"×0.003". A braided sheath for the lead engaging member 12 formed from about 16 flat wires was found to be suitable for specific applications. In addition, an outer diameter of the lead engaging member 12 of 0.016" in the stretched configuration and about 0.045" in a substantially relaxed configuration were found to be suitable for specific applications. Preferably, the tip of the lead locking device is less than about 0.017 inch. In a preferred embodiment, the mandrel 14 tapers from the proximal end to the distal end. Thicknesses of the mandrel 14 ranging from about 0.020" to about 0.011" going from the proximal end to the distal end were found to be suitable for particular applications. The lead locking device 10 may also include a fillet provided at the interface between the outer hypotube 32 and the lead engaging member 12, although it is currently more preferred not to include a fillet. A suitable material for the fillet, if included, is glue or solder.

As one may see in another preferred embodiment illustrated in FIGS. 3A and 3B, the lead locking device 10' includes a distal band 46 attached to the distal end 22'. FIG. 3A is an enlarged view of a section of the lead locking device 10', except the distal end 46 replaces the solder tip 24 illustrated in FIG. 2. The distal band 46 is disposed over a distal portion 48 of the lead engaging member 12. Preferably, the distal band 46 and the distal portion 48 are joined together. The distal band 46 and distal portion 48 of the lead engaging member 12 are preferably joined together by epoxy disposed therebetween. The epoxy permeates the braid of the distal portion 48 of the lead engaging member 12 up to a wick length 47. More preferably, an epoxy plug 49 is formed at the distal end of the lead locking device 10', mechanically locking the distal band 46 to the lead engaging member 12 and mandrel 14. The epoxy plug reduces fraying of the wires forming the braided lead engaging member if one, or some, of the wires break. In other embodiments, it is also suitable to join the distal band 46 and the distal portion 48 by other adhesives, soldering, welding or by crimping. A suitable material for the distal band is an alloy of platinum and iridium (preferably 90% Pt and 10% Ir).

FIG. 4 is a schematic illustration of a lead locking device 10" which is similar to the lead locking device 10, but it has a latching mechanism 50 instead of a press-fit type of latching mechanism 18. In the lead locking device 10", the loop handle 16" is similar to the loop handle 16. The loop handle 16" forms a proximal loop 36' an end 38' that is twisted around another portion of the mandrel 14. A proximal loop hypotube 42' is preferably disposed over the twisted end 38' of the loop handle 16" which is crimped. In the preferred embodiment of the lead locking device 10" the latching mechanism 50 has a portion 52 attached to the proximal end of the lead engaging member 12. Preferably, the latching mechanism 50 also has a portion 54 attached to a proximal portion of the mandrel 14 that provides a male connector. The portion 52 attached to the proximal end 20 of the lead engaging member 12 is selectively and removably attachable to the portion 54 attached to the proximal end of the mandrel 14. More preferably, the portion 52 attached to the proximal end 20 of the lead engaging member 12 and the portion 54 attached to the proximal portion of the mandrel 14 cooperatively form a snap-fit latching mechanism. More preferably, the portion 52 attached to the proximal end 20 of the lead engaging member 12 is a first hypotube having a detent 56 defined by an inner surface of the first hypotube 52. Preferably, the portion 54 attached to a proximal portion of the mandrel 14 has an outer surface that defines an indent 58. The detent 56 is secured within the indent 58 in a latched configuration of the latching mechanism 50, thus holding the lead engaging member in a stretched configuration. In the preferred embodiment, a second hypotube 60 is slidably disposed over the mandrel 14 and arranged concentrically with the first hypotube 52 such that a proximal portion 20 of the lead engaging member 12 is disposed therebetween. The concentric arrangement of second hypotube 60, the proximal portion 20 of the lead engaging member 12 and the first hypotube 52 are securely attached by at least one of adhesive material, welding and crimping, but preferably by crimping, to form a female connector. Although the lead locking device 10" has a distal tip 24 as in the lead locking device 10, a distal band such as in the lead locking device 10' may also be used in this embodiment. The material of the first and second hypotubes 52 and 60 is preferably stainless steel. The material of the portion 54 is preferably stainless steel or a polymer. A fillet may also be provided at the interface of the first hypotube 52 and the proximal end 20 of the lead engaging member 12. The fillet, if used, is preferably glue or solder.

In operation of the lead locking device 10, the user slides the portion 26 of the press-fit type of latching mechanism 18 that is attached to the proximal end 20 of the lead engaging member 12 along the mandrel 14 in a direction from the distal tip 24 towards the loop handle 16 until the inner hypotube 30 and outer hypotube 32 are positioned approximately at the center of the crimp 28. The crimped portion 28 of the mandrel 14 provides resistance to sliding the inner hypotube 30 and outer hypotube 32 thereon. Similarly, once the inner hypotube 30 and outer hypotube 32 are positioned over the crimped portion 28 of the mandrel 14, the crimped portion of the mandrel 14 provides a resistive force which cancels the restoring force provided by the lead engaging member 12 in the stretched configuration, thus holding it in place.

The lead engaging member 12 is disposed in a lumen defined by a lead, for example, a pacing lead for a pacemaker. Pacing leads are coiled, thus forming a lumen therein. The lead engaging member 12 is inserted into the lead lumen until it is disposed along at least about 30% of the length of the pacing lead, and more preferably substantially along the entire length of the pacing lead. The surgeon, or other user of the lead locking device 10, releases the press-fit type of latch mechanism by sliding the inner hypotube 30 and outer hypotube 32 combined unit toward the distal tip 24. The additional force provided by the surgeon overcomes the resistive force provided by the crimped portion 28 of the mandrel 14. The lead engaging member 12 thus acquires a substantially relaxed configuration such that it has a larger diameter than when it was in a stretched configuration. The wider diameter of the lead engaging member 12 acts to frictionally engage and lock the lead engaging member 12 to an inner surface of the lumen of the lead, along at least about 30%, and more preferably substantially the entire length of the lead. Flat braided wires in the lead engaging member 12 enhance the quality of the grip between the lead engaging member 12 and the inner portions of the lead. Furthermore, the flexibility of the lead engaging member 12 compensates for variations in the shape and size of the lumen of the lead to ensure a good grip along an extended portion of the lumen.

Traction is then applied to the mandrel 14, which may be primarily provided by applying traction to the loop handle 16. Since the lead locking device 10 is locked along at least about 30%, and more preferably substantially the entire length of the lead, the traction is distributed over an extended portion of the lead rather than being applied in a small local region. In addition, by engaging the lead along at least about 30% of the lumen of the lead to include at least a proximal portion and at least a distal portion of the lead, traction forces are distributed to at least a proximal portion and a distal portion of the lead. By distributing the traction force over an extended portion of the lead, distortions, disruptions and breakage of the lead are reduced.

The lead locking device 10 may also be unlocked, and removed, from the lead prior to removing the lead from the patient's body. This may be done to abort the operation, remove and reconfigure the lead locking device 10, remove the lead locking device 10 and replace it with another device, or to remove the lead locking device to apply other methods and techniques. To release the lead locking device from the lead, the surgeon slides the inner hypotube 30 and outer hypotube 32 arrangement towards the proximal end, away from the distal tip 24, thus restretching the lead engaging member 12.

In the preferred embodiment, the flat wires of the braided sheath of the lead engaging member 12 lock along an extended length of the lead. The lead locking devices 10' and 10" operate in a manner similar to that of lead locking device 10. After inserting the lead locking device 10" into the lumen of a lead, the surgeon applies traction to the mandrel 14, which may be primarily applied through the loop handle 16". The lead locking device 10" may be removed from the lead either before or after removal of the lead from the patient's body by sliding the first hypotube 52 away from the distal tip 24 towards the loop handle 16" such that the first hypotube 52 forms a snap-fit with the portion 54 attached to the mandrel 14. Once the detente 56 is secured within the indent 58, the lead engaging member 12 is held in a stretched configuration, thus having a narrower outer diameter than in the relaxed configuration. The surgeon then applies traction to the lead locking device 10″ through the mandrel 14 to remove the lead locking device 10″ from the lead. Although the preferred embodiment of the lead locking device 10 has a press-fit mechanism, and the lead locking device 10″ has a snap-fit mechanism, the general concepts of the invention are not limited to prestretching the lead engaging member in only these ways. One skilled in the art would recognize, based on the above teachings, that numerous other mechanisms may be used.

Figure 5A:
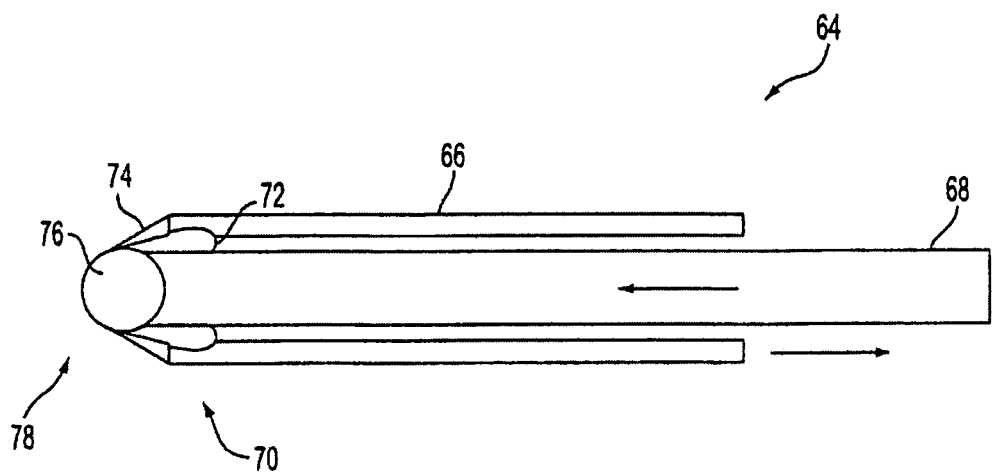
FIG. 5A and FIG. 5B illustrate two configurations of a second embodiment of the lead locking device according to the invention.
Figure 5B:
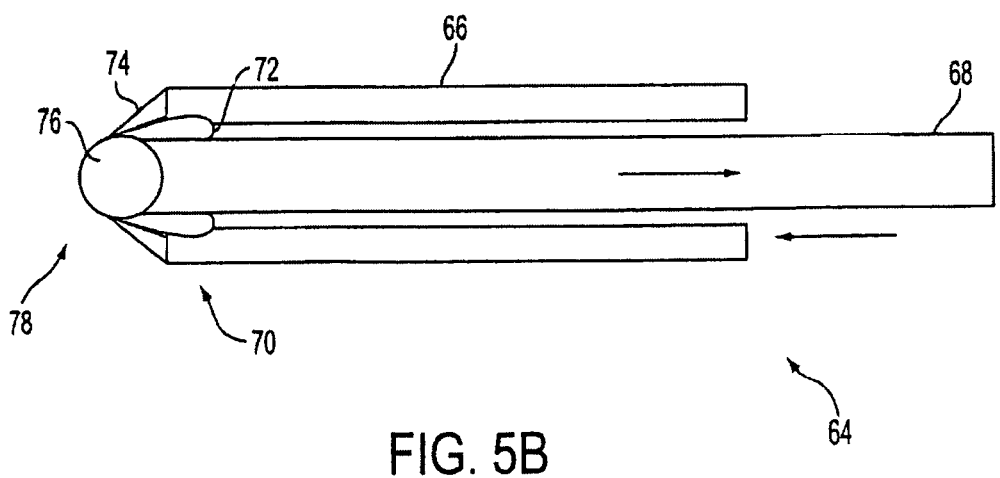

FIGS. 5A and 5B show a second preferred embodiment of the invention. The lead locking device 64 has a lead engaging member 66 and a mandrel 68. The mandrel 68 is disposed in a lumen defined by the lead engaging member 66 and attached at the distal end 70 of the lead engaging member 66. The lead engaging member 66 is preferably attached to the mandrel 68 by adhesive material 72. A fillet 74 is attached at an interface between the lead engaging member 66 and the distal end 70 of the mandrel to form a smoother fit. In addition, a spherical element 76 may be attached to the distal tip 78 of the lead locking device 64 in order to form a smooth and rounded tip. In the second preferred embodiment, the lead engaging member 66 is an elastic material such as a rubber material. FIG. 5A shows the lead engaging member in a stretched configuration. The lead locking device 64 may also employ a press-fit or latching mechanism as in the lead locking devices 10 and 10″, or may be used without such a mechanism in which case the surgeon holds the lead locking member 66 in a stretched configuration. Similarly, the lead locking devices 10 and 10″ may also be used without the press-fit and latching mechanisms, in which case the surgeon may hold the braided lead locking member in a stretched configuration and release it for it to acquire a substantially relaxed configuration.

FIG. 5B shows the lead engaging member 66 in a substantially relaxed configuration in which it has a greater outer diameter than in the stretched configuration, as illustrated in FIG. 5A.

The lead locking device 64 is used in a similar manner to the lead locking devices 10, 10′, and 10″. The surgeon stretches the lead engaging member 66, inserts the lead engaging member 66 into a lumen defined by a lead, and releases the lead engaging member 66 such that it takes on a substantially relaxed configuration. The lead engaging member 66 in the stretched configuration has a narrower outer diameter than the diameter of the lumen. Upon releasing the lead engaging member 66 it engages the lead lumen and locks onto the lead, along at least 30%, and more preferably along the entire length of the lead since it has a diameter substantially equal to or greater than the lumen diameter in the relaxed configuration. The surgeon then applies traction to the mandrel 68 which may include an attached loop handle. The lead locking device 64 is similarly removable from the lead, either before or after the lead is removed from the patient's body.

Figure 6:
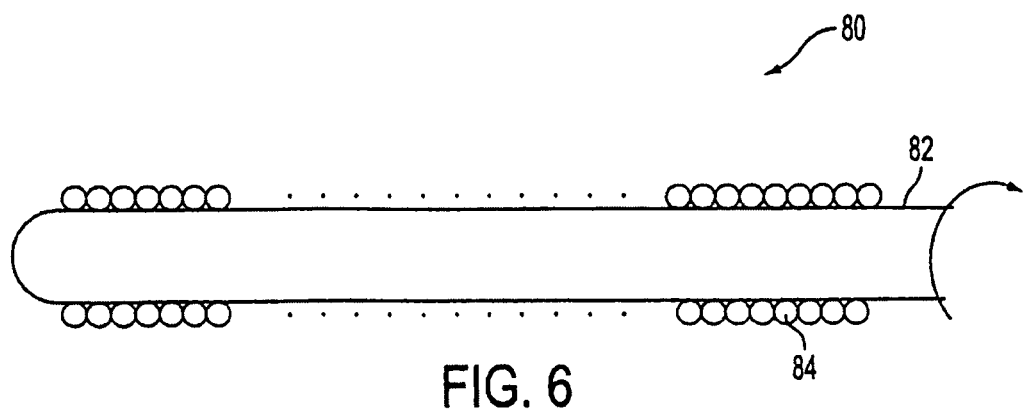
FIG. 6 illustrates a third embodiment of a lead locking device according to the invention.

FIG. 6 is an illustration of the third embodiment of the invention. The lead locking device 80, according to the third embodiment has a mandrel 82 with a coil 84 wrapped therearound. The coil 84 is preferably metal wire. More preferably, the coil 84 is stainless steel wire. The lead locking device 80 has a tightly wrapped configuration with an outer diameter less than the lumen diameter when it is inserted into the lumen defined by a lead. After the surgeon inserts the lead locking device 80 such that the coil 84 extends substantially along the entire length of the lead, the surgeon rotates the mandrel 82 about a longitudinal axis so as to cause the coil 84 to partially unwind, thus obtaining a loosely wound configuration with an increased diameter. The coil 84 in the loosely wound configuration locks onto the lead along at least about 30%, and more preferably along substantially the entire length of the lead by friction or other contact forces. The surgeon then applies traction to the mandrel 82 to remove the lead from the patient's body. The lead locking device 80 can be removed from the lead either before or after the lead is removed from the patient's body by rotating the mandrel in a direction to cause the coil 84 to wind more tightly, thus obtaining a tightly wound configuration. The surgeon then can remove the lead locking device 80 from the lead by applying traction to the mandrel 82 without significant traction being applied to the lead.

Figure 7A:
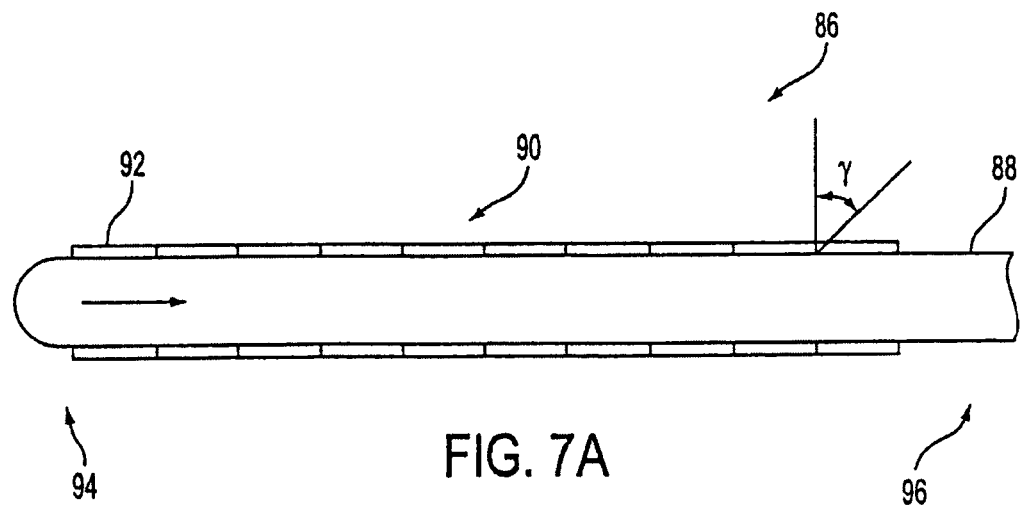
FIG. 7A and FIG. 7B illustrate two configurations of a lead locking device according to a fourth embodiment of the invention.
Figure 7B:
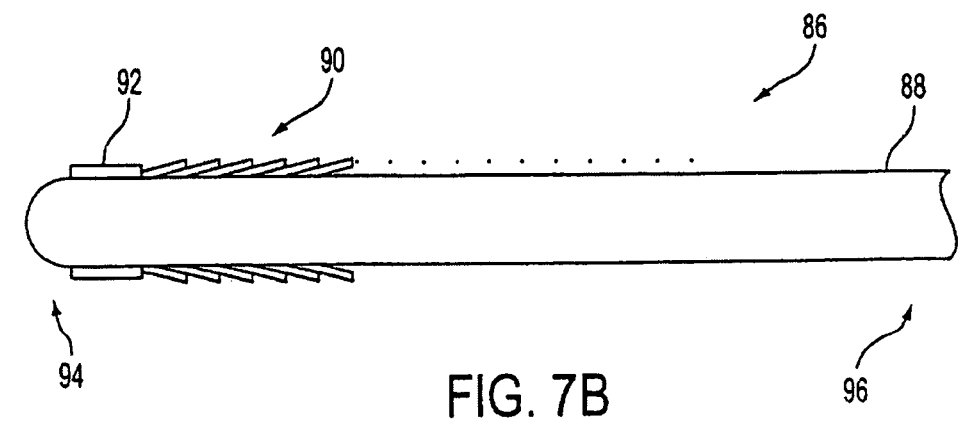

FIGS. 7A and 7B show a fourth embodiment of a lead locking device according to the invention. The lead locking device 86 according to the fourth embodiment has a mandrel 88 and a helical ribbon 90 wrapped around the mandrel 88. The most distal portion 92 of the helical ribbon 90 is attached to the mandrel 88, preferably by adhesive or welding. The interface between adjacent portions of the helical ribbon 90 preferably has an up-slope from the distal end 94 to the proximal end 96 of the mandrel which is an acute angle γ. Preferably, the angle between all adjacent portions of the ribbon meet at a substantially uniform angle γ. In operation, the surgeon inserts the lead locking device 86 into a lumen defined by a lead until the helical ribbon 90 extends along at least about 30%, and more-preferably substantially along the entire lead. The surgeon applies traction to the mandrel 88 which causes the helical ribbon 90 to partially overlap itself, as illustrated in FIG. 7B. The outer diameter of the lead engaging member 90 in the configuration illustrated in FIG. 7B is larger than that illustrated in FIG. 7A. Consequently, the lead engaging member 90 locks onto the lead along at least 30%, and more preferably substantially along the entire length of the lead.

The surgeon can remove the lead locking device 86 from the lead, either before or after removing the lead from the patient's body. In order to remove the lead locking device 86 from the lead, the surgeon pushes on the mandrel 82 towards the distal tip 94. The lead engaging member 90 then reacquires the configuration illustrated in FIG. 7A, which permits the surgeon to apply traction on the lead 88 to remove it from the lead without it transferring significant traction to the lead.

Each of the lead locking devices according to the third embodiment 80 and the fourth embodiment 86 may also have a press-fit or a latch mechanism and may have a loop handle as in the first and second embodiments.

Figure 8:
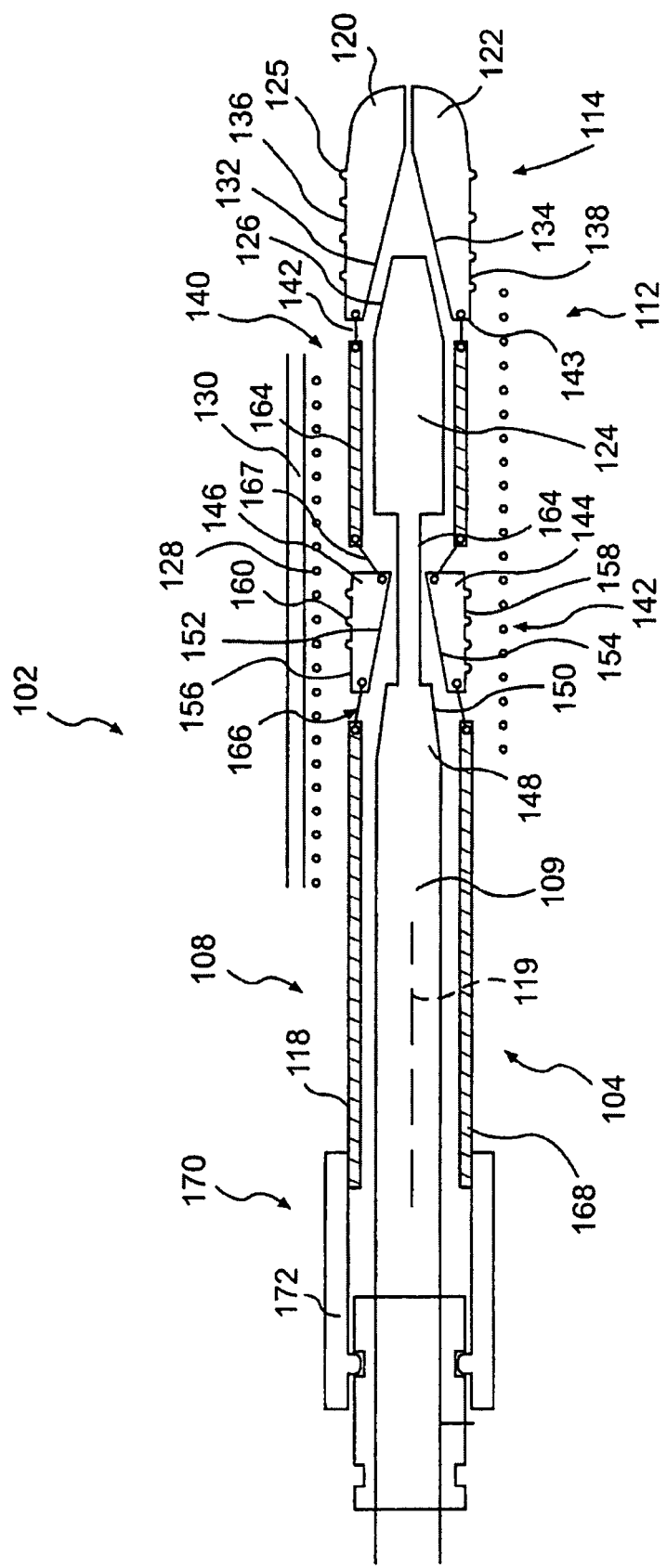
FIG. 8 illustrates a fifth embodiment of a lead locking device according to the invention with a portion cut away.
Figure 9:
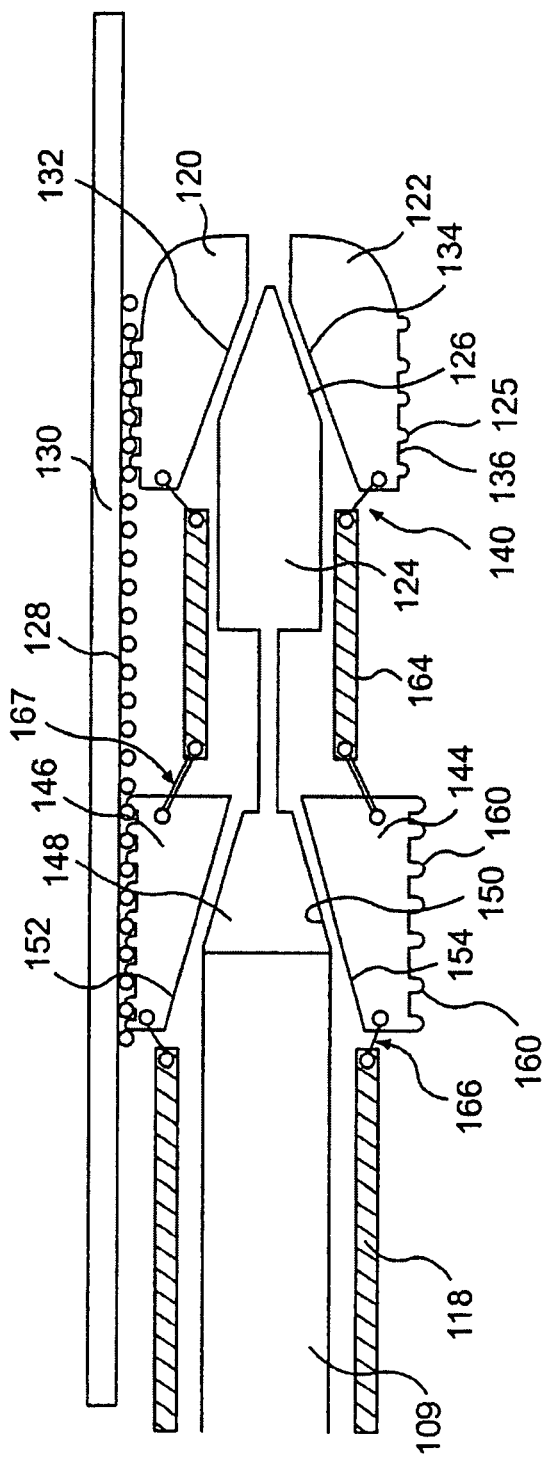
FIG. 9 is a blown-up view of a section of FIG. 8.
Figure 12:
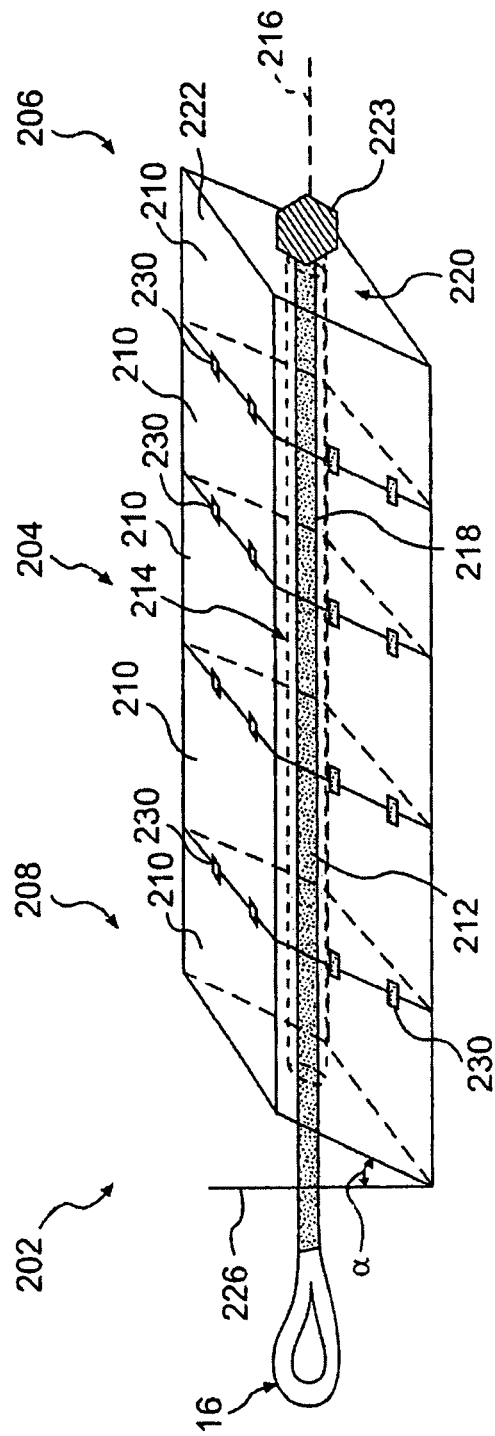
FIG. 12 illustrates a sixth embodiment of a lead locking device according to the invention.
Figure 15:
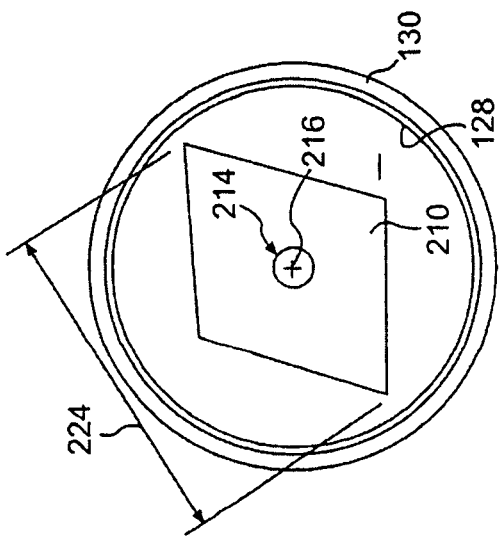
FIG. 15 is an end view of the embodiment of FIG. 12.

FIGS. 8-10 show a fifth embodiment of a lead locking device according to the invention. The lead locking device 102 according to the fifth embodiment includes a lead insertion member 104 and a mandrel 109. The lead insertion member 104 has a lead engaging assembly 114. The lead insertion member 104 has a proximal end 108 and a distal end 112 extending along a longitudinal axis 119 between the distal 112 end and the proximal end 108. The mandrel 109 is disposed in the lumen 118 and is slidable therein and extends along substantially the entire length of the lumen and protrudes beyond the most proximal end of the lead insertion member 104. The mandrel 109 includes a distal cam 124 for actuating the lead engaging assembly 114. The distal cam 124 of the mandrel 109 has a conically shaped outer surface 126. The lead engaging assembly 114 has a first configuration while being inserted into the lumen 128 of the lead 130 and a second configuration while engaging the lead from within the lumen of the lead.

The lead engaging assembly 114 includes at least two expansion jaws 120, 122 that in the first configuration generally define a cylindrical body. Preferably, the two expansion jaws 120, 122 include conically shaped inner surfaces 132, 134 that correspond to the conically shaped outer surface 126 of the distal cam 124 of the mandrel 109 such that engagement of the outer surface of the distal cam 124 with the inner surfaces of the two expansion jaws 120, 122 causes the expansion jaws 120, 122 to each translate radially outward with respect to the longitudinal axis 119 of the lumen 118 to engage the lead when in the second configuration. That is, as the outer surface 126 of the distal cam 124 of the mandrel 118 and the inner surfaces 132, 134 of the two expansion jaws 120, 122 move relative to each other such that they are in sliding, wedge-type contact, each expansion jaw is caused to translate radially outward and engage the lead 130. Preferably, the outer surfaces 136, 138 of the two expansion jaws include detents 125 for engagement with the lead 130 when the lead engaging assembly 114 is in the second configuration. Preferably, the forward end of each expansion jaw 120, 122 has generally a rounded configuration to facilitate entry into the lumen of the lead when the lead engaging assembly 114 is in the first configuration. The other end 143 of the expansion jaws 120, 122 are resiliently connected, with a resilient connector 140, to the distal end of the lumen of the lead insertion member so that when the mandrel 109, and specifically the distal cam 124 of the mandrel, is backed away from the two expansion jaws in the second configuration, the resilient connector 140 biases the two expansion jaws back to the first configuration. Preferably, the resilient connector includes springs 142 connecting the other ends 143 of the expansion jaws 120, 122 to a connector section 164 of the lead insertion member 104.

The lead locking device of the fifth embodiment may also include a second lead engaging assembly 142 disposed between the distal end 112 and the proximal end 108 of the lead insertion member 104, the second lead engaging assembly 142 operating in substantially the same manner as the first mentioned lead engaging assembly 114. That is, the second lead engaging assembly 142 has a first configuration while being inserted into the lumen of the lead and a second configuration while engaging the lead from within the lumen of the lead. The second lead engaging assembly 142 includes at least two expansion jaws 144, 146 that, in the first configuration, substantially define a portion of a cylindrical body that is disposed around the mandrel 109. Each of the two expansion jaws 144, 146 translate radially outwardly from the longitudinal axis to engage the lead 130 when in the second configuration. The two expansion jaws 144, 146 are caused to translate radially outwardly by a conically-shaped outer surface 150 of a proximal cam portion 148 of the mandrel 109. That is, as with the first-mentioned lead engaging assembly member 114, the two expansion jaws 144, 146 of the second engagement member 142 include conically-shaped inner surfaces 152, 154 that correspond to the conically-shaped outer surface 150 of the proximal portion 148 of the mandrel 109, such that interfering engagement (i.e. wedge-type sliding contact) of the outer surface of the proximal portion 148 with the inner surfaces 152, 154 of the two expansion jaws 144, 146 of the second engagement assembly 114 causes the two expansion jaws 144, 146 to each translate radially outwardly (i.e., expand) with respect to the longitudinal axis 119 of the lumen 118. The outer surfaces 156, 158 of the two expansion jaws 144, 146 may include detents 160 for engagement with the lead 130 when the second engagement assembly 142 is in the second configuration. The second engagement assembly 142 and first mentioned engagement assembly 114 each move from the first configuration to the second configuration substantially simultaneously. That is, the first-mentioned engagement assembly 114 and the second engagement assembly 142 each translate radially outwardy simultaneously as the distal cam 124 and proximal cam 148 of the mandrel 109, respectively, engages the conically-shaped inner surfaces of each member. The first-mentioned lead-engaging assembly 114 and the second lead engaging assembly 142 have a maximum transverse diameter in the first configuration that is less than substantially all diameters of the lead 130 along substantially the entire length of the lead, and the first-mentioned lead engaging assembly 114 and the second lead engaging assembly 144 have a transverse diameter in the second configuration that is at least substantially equal to diameters of the lumen of the lead.

As shown in FIGS. 8 and 9, the distal cam 124 and proximal cam portion 148 of the mandrel 109 are connected to each other via a reduced diametric section 162 that extends from the end of the proximal cam portion 148 to the rearward end of the distal cam 124. When the second lead engagement assembly 142 is in the first configuration, the two expansion jaws 144, 146 are generally in partial surrounding relation to the reduced diametric section 162. To accommodate the second lead engagement assembly 142, the lead insertion member 104 has a distal connector section 164 and a proximal connector section 168 of the lead insertion member 204. The first-mentioned lead engaging assembly 114 is thus attached to the distal connector section 164, as describe above, and the second lead engaging assembly 148 is attached in a similar manner to the proximal connector section 168. That is, the two expansion jaws 144, 146 of the second engagement assembly 142 are resiliently connected, with resilient connectors 166, to the proximal connector section 168 of the lead insertion member 104. The resilient connector 166 may be is the same as the resilient connector 140 describe above for the first-mentioned lead-engaging assembly 114. The distal connector section 164 and proximal connector section 168 are portions of a generally tubular connector that has radially opposed slots therein to accommodate the opposing expansion jaws 144 and 146.

The longitudinally opposing ends of the expansion jaws 144, 146 of the second lead engaging assembly 142 may be similarly resiliently connected, with resilient connectors 167, to the distal connector section 164 of the lead insertion member 104, if desired.

As shown in FIG. 10, the two expansion jaws 144, 146 of the second lead engaging assembly 142 are rotated approximately 90 degrees relative to the two expansion jaws 120, 122 of the first-mentioned lead engaging assembly 114. Thus, when each of the two expansion jaws of each engagement assembly translates radially outwardly to the second configuration, an engagement force is applied to the lead in generally four directions, as shown by the arrows in FIG. 10.

As will be understood by those skilled in the art, the fifth embodiment described above is not limited to two lead engaging assemblies 114 and 148. Rather, any number of lead engaging assemblies is contemplated. Also, the length of the lead engaging assemblies 114, 142, and any other lead engaging assemblies that may be included, is such that the lead engaging assemblies lock (or engage) at least about 30% of the length of the lead 130 up to substantially the entire length of the lead. Further, the 30% of the length may include at least a portion of a proximal end and at least a portion of a distal end of the lead 130. In yet another construction of this embodiment, the lead engaging member may have at least a set of distal expansion jaws and a set of proximal expansion jaws so that the lead engaging member can engage the lead at both a distal and a proximal end of the lead.

The lead engaging member 114 has two expansion jaws 120 and 122 and the lead engaging member 142 has two expansion jaws 144 and 146 in the embodiment illustrated above. One should understand from the teachings herein that greater than two expansion jaws for the lead engaging members 114 and 142 may be used without departing from the scope of the invention.

FIG. 11 is a schematic illustration of a latching mechanism 170 used to fix the position of the mandrel 109 such that the lead engaging assemblies 114, 142 remain in first and second configurations. In an illustrative embodiment, the latching mechanism 170 has a portion 172 attached to the most proximal end 108 of the lead insertion member 104. Preferably, the latching mechanism 170 also has a portion 174 attached to a proximal portion of the mandrel 109, the portion 174 providing a male connector. Preferably, the portion 174 forms a bore 182 therethrough and is disposed and fixed on the mandrel 109. The portion 172 attached to the proximal end 108 of the lead insertion member 104 is selectively and removably attachable to the portion 174 attached to the proximal end of the mandrel 109. More preferably, the portion 172 attached to the proximal end 108 of the lead insertion member 104 and the portion 174 attached to the proximal portion of the mandrel 109 cooperatively form a snap-fit latching mechanism. More preferably, the portion 172 attached to the proximal end 108 of the lead insertion member 104 is a first hypotube having a detent 176 defined by an inner surface of the first hypotube 172. Preferably, the portion 174 attached to a proximal portion of the mandrel 109 has an outer surface that defines at least two indents 178, 180. The detent 176 is secured within the indent 178 in a latched configuration of the latching mechanism 170, thus holding the lead insertion member in a position such that the conically shaped outer surfaces 126, 150 of the distal and proximal portions 124, 148 of the mandrel are not engaged with the first and second engagement assemblies 114, 142, respectively (i.e., each engagement assembly is in the first, relaxed configuration). When actuated by the user, the mandrel 109 is forced inward (i.e., to the right as shown in FIG. 11) (or the lead insertion member 104 is forced rearward, which is to the left as shown in FIG. 11) so that the detent 176 is secured within the indent 180, thus holding the mandrel 109 in a position such that the conically shaped outer surfaces 126, 150 of the distal and proximal cams 124, 148 of the mandrel are engaged with the first and second engagement assemblies 114, 142, respectively (i.e., each engagement assembly is in the second, deployed configuration). Although the detent 176 and indents 178, 180 are shown on the first hypotube 172 and portion 174, respectively, the latching mechanism would operate in the same manner with the two detents formed on the portion 174 and an indent formed on the hypotube 172. The material of the hypotube 172 is preferably stainless steel. The hypotube 172 is preferably welded, soldered, glued, or otherwise fixedly attached to the lead insertion member 104. The material of the portion 174 is preferably stainless steel or a polymer and is fixedly attached to the mandrel 109 via welding, soldered, glued, or other fastening means.

In operation of the lead locking device 102, the user secures the detent 176 within indent 178 of the portion 174 of the latching mechanism 170. In this position, the first and second lead engagement assemblies 114, 142, respectively, are in the first configuration and the lead locking device 102 is inserted into the lumen 128 of the lead 130. The lead insertion member 104 is inserted into the lead lumen 118 until it is disposed along at least about 30% of the length of the pacing lead 130.

The surgeon, or other user of the lead locking device 102, applies an inward longitudinal force to the mandrel via the proximal loop (or a rearward axial force to the hypotube 172) so that the detent 176 is secured within indent 180 of the portion 174. In this manner, the distal and proximal cams 124, 148 of the mandrel 109 moved forward relative to the lead insertion member 104 and lead engagement assemblies 114, 148 to engage the inner surfaces of the first and second lead engagement assemblies 114, 142. The lead engagement assemblies 114, 142 thus translate radially outward (i.e., expand) to engage the lead in the second configuration. The detents 125, 160 of the respective lead engagement assemblies 114, 142 ensure a good grip along the engaged portion of the lumen.

Traction is then applied to the mandrel 109, which may be primarily provided by applying traction to the proximal loop handle 16. Since the lead locking device 102 is locked (and engages) along at least 30% of the length of the lead 130, the traction is distributed over an extended portion of the lead rather than being applied to a single, localized region. In addition, by engaging the lead along at least a proximal portion and at least a distal portion of the lead, traction forces are distributed along the proximal and distal portions of the lead. By distributing the traction force over an extended portion of the lead, distortions, disruptions and breakage of the lead are reduced.

The lead locking device 102 may also be unlocked and removed from the lead prior to removing the lead from the patient's body. This may be done to abort the operation, remove and reconfigure the lead locking device 102, remove the lead locking device 102 and replace it with another device, or to remove the lead locking device to apply other methods and techniques. To release the lead locking device from the lead, the surgeon positions the detent 176 within the indent 178, thus backing the mandrel 109 away from the first and second lead engagement assemblies 114, 142 so that each are returned to the first configuration.

FIGS. 12-15 show a sixth embodiment of the invention. The lead locking device 202 according to the sixth embodiment includes a lead engaging member 204 having a distal end 206 and a proximal end 208. The lead engaging member 204 includes a series of juxtaposed sections 210, each section forming a through hole 212 and each through hole being aligned with an adjacent through hole 212 of an adjacent member to define a continuous bore 214 extending along a longitudinal axis 216 between the distal end 206 and the proximal end 208. Preferably, each section 210 is a block, although any shape that includes at least two extreme points may be used. The material of the sections 210 is preferably stainless steel. A mandrel 218 is disposed in the bore 214 and is fixedly attached to at least one of said sections 210 of the lead engaging member. Preferably, the distal end 220 of the mandrel is fixedly attached, by welding, soldering, or other fastening means, to a distal section 222 on an outer surface thereof. The mandrel is shown fastened to the distal section 222, the fastener being generally indicated by numeral 223. The mandrel 218 extends along substantially the entire length of the bore and protrudes beyond the most proximal end of said lead engaging member 204. The lead engaging member 204 has a first configuration while being inserted into the lumen of the lead 130 and a second configuration while engaging the lead from within the lumen 128 of the lead.

Each of the sections 210 of the lead engaging member 204 has a maximum transverse dimension 224 (shown in FIG. 15) that is less than substantially all of the diameters of the lumen 128 of the lead 130 along substantially the entire length of the lead so that the lead engaging member can be inserted into the lumen 128 of the lead 130 while in the first configuration.

Each of the sections 210 of the lead engaging member 204 is further skewed, by an angle α (FIG. 12) with respect to a normal 226 of the longitudinal axis 216. Further, each section 210 of the lead engaging member 204 is in sliding contact with an adjacent section, and each of the sections is connected to an adjacent section with a plurality of connectors 230 capable of transmitting torque from one section to an adjacent section. The connectors 230 may be flexible connectors. The connectors 230 may be disposed externally, as shown, or internally on the contacting faces of each section.

When a torque is applied to the mandrel 218 via the proximal end loop 16, the fastener 223 transmits the applied torque to the distal section 222 to which it is fastened. Because each section is connected to adjacent sections with the flexible members 230, a resulting "twist" of the lead engaging member 204 results. Further, each section 210 is skewed from a normal 226 to the longitudinal axis 216 of the bore (and mandrel 220). Thus, as torque is applied and the series of section 210 is twisted. Each section 210 is substantially inhibited from rotation by the adjacent element to cause some of the elements to radially deflect with respect to the longitudinal axis 216. As a result of this deflection, a "chain reaction" occurs and the series of sections 210 "bundle up" to increase the overall diametric dimension of the lead engaging member 214. The overall diametric dimension is defined as the dimension from the two most extremely deflected portions 210, and is indicated as reference numeral 228 (FIGS. 13 and 14). As seen, the overall diametric dimension 228 when the lead engaging member 204 is in the first configuration (FIG. 13) is less than the overall diametric dimension when the lead engaging member is in the second configuration (FIG. 14). When a sufficient torque is applied, the radially deflected and "bundled up" sections 210 engage the lumen 128 of the lead 130 in the second configuration. The lead engaging member 204 has an overall transverse maximum dimension 228 in the second configuration that is at least substantially equal to diameters of the lumen 128 of the lead 130 along substantially the entire length of the lead. Preferably, the lead engaging member 204 engages the lead 130 along at least about 30% of the entire longitudinal length of the lumen of the lead. Preferably, at least 30% of the entire longitudinal length of said lumen of said lead includes at least a portion of a proximal end and at least a portion of a distal end of the lumen of the lead. Preferably, the lead engaging member 204 engages the entire length of the lumen 128 of the lead 130.

In operation of the lead locking device 202 of the sixth embodiment, the lead engaging member 204 is inserted into the lumen 128 of the lead 130 that is implanted in a patient's body. The lead engaging member 204 is inserted while in the first configuration, where the lead engaging member is in the relaxed condition, i.e., no torque is applied to the mandrel 218. The lead engaging member is inserted into the lead lumen until it is disposed along at least about 30% of the length of the lead, and more preferably substantially along the entire length of the lead. The surgeon, or other user, then applies a torque to the lead engaging member 204 (via the proximal end loop 16 of the mandrel 218) which causes the lead engaging member to have an overall diametric dimension 228 that is substantially equal to an inner diameter of the lumen 128 of the lead 130. Thus, the lead engaging member 204 engages the lead 130 along substantially the entire longitudinal length of the lead. Then, traction is applied to the lead locking device 204 via the proximal end loop 16.

FIGS. 16-19 show a seventh embodiment of the invention. The lead locking device 302 according to the seventh embodiment includes a hypotube 306 including a plurality of openings 308 formed therein along the length thereof. The openings 308 can be circular holes, slots 309, or other shapes. The hypotube 306 extends along a longitudinal axis 316 between a distal end 310 and a proximal end 312 thereof. A lead engaging member 304 is disposed within the hypotube 306 and includes a plurality of bristles 314 extending from a mandrel 318. In a free state (i.e., prior to being inserted into the hypotube 306), the radial dimension 305 is greater than the radial dimension of the lumen 130 of the lead 128. After being inserted into the hypotube 306., the bristles 314 are thus resiliently biased in the outward radial direction from the longitudinal axis 316. Preferably, all of the bristles 314 generally point in the same direction with the end attached to the mandrel being forward of the distal end 324 of each bristle. Preferably, the material of the bristles 314 is stainless steel, however, rigid plastic can also be used. The lead engaging member 304 is disposed generally along the longitudinal axis 316 and extends along substantially the entire length of the hypotube 306 and protrudes beyond the most proximal end of the hypotube.

The lead engaging member 304 has a first configuration while being inserted into a lumen 118 of a lead 130 and a second configuration while engaging said-lead from within said lumen 128 of said lead 130. In the first configuration, the bristles 314 are disposed within the hypotube 306 (FIG. 18), and the outer diameter of the hypotube 306 is less than the diameters of the lumen 128 of the lead 130. In the first configuration, because the bristles 314 are resiliently biased in the outward radial direction, the bristles possess an internal restoring force that biases the bristles against the inside surface 320 of the hypotube 306. In the second configuration, the bristles 314 protrude from the plurality of openings 308 and the distal ends 324 thereof have a transverse diametric dimension that is at least substantially equal to diameters of said lumen of said lead along substantially the entire length of said lead so that some of the distal ends 324 engage the lead 130. Preferably, a majority of distal ends 324 engage the lead 130.

As with previous embodiments, bristles 314 of the lead engaging member 314 engage the lead 130 along at least about 30% of the entire longitudinal length of the lumen 128 of the lead 130. Preferably, the at least 30% of the entire longitudinal length of the lumen of the lead includes at least a portion of a proximal end and at least a portion of a distal end of the lumen of the lead. Preferably, the bristles 314 of the lead engaging member 304 engage substantially the entire length of said lumen of said lead.

The lead engaging member 304 may be locked into the first and second configurations using a latching mechanism 170, which may be the same latching mechanism described in the fifth embodiment (FIGS. 8-1).

Figure 16:
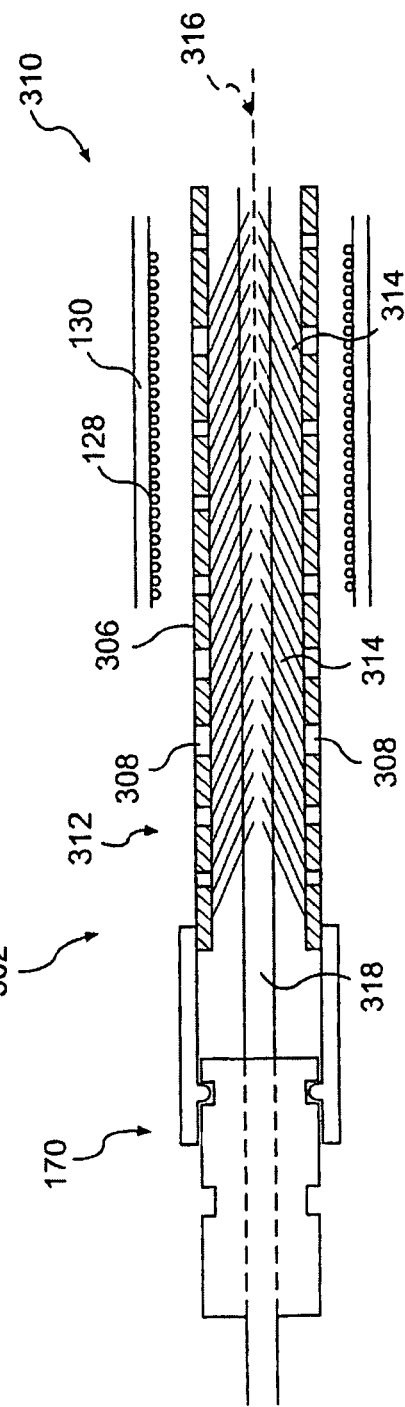
FIG. 16 illustrates a seventh embodiment of a lead locking device in a relaxed configuration.

In operation of the lead locking device 302, the surgeon or other user inserts the lead engaging member 314 into the hypotube 306 and then inserts the lead locking device 302 into the a lead 130 (see FIGS. 17 and 18). At this point, the lead engaging member 304 is in the first configuration and the bristles 314 are disposed within the hypotube 318 (FIGS. 16 and 18). The surgeon then applies an axial force to the mandrel 318 to pull the lead engaging member 304 in the opposite direction to the direction in which the lead engaging member was inserted into the hypotube 306. As the lead engaging member 304 moves backwards (to the left as shown in FIGS. 16-19), the bristles 314, which are biased outward under a restoring force in the first configuration, "find" an opening 308, and as the mandrel is pulled in the direction of the arrow (FIG. 19), the bristles protrude from the openings to engage the lumen 128 of the lead 130. The lead engaging member 304 is thus in the second configuration, where the overall diametric dimension of the distal ends 324 of the bristles 314 is substantially equal to an inner diameter of the lumen (FIG. 19). The lead engaging member 314 preferably engages the lead 130 along substantially the entire longitudinal length of said lead 130. The surgeon then applies traction to the lead locking device 302 to remove the lead 130 from a patient.

To remove the lead locking device 302 from the lead 130, the user applies an axial force to the lead engaging member 304 in the opposite direction to that for engaging it so that the distal ends 324 of the bristles 314 retract from the openings 308 and are disposed within the hyptotube 306 (i.e., the first configuration). The user then removes the lead locking device 302 from the lumen 128 of lead 130.

FIGS. 20-21 show an eighth embodiment of the invention. The lead locking device 402 according to the eighth embodiment includes a lead engaging member 404 having a distal end 410 and a proximal end 412. The lead engaging member 404 includes a series of radially expandable elastic members 414 disposed around a mandrel 418, which extends along a longitudinal axis between the distal end 410 and the proximal end 412. The mandrel protrudes beyond the most proximal end of the lead engaging member.

In the eighth embodiment of the invention, the series of elastic members 414 may include a series of radially-expandable, elastic, ring sections that are substantially relaxed in the first configuration and radially expanded under a compressive force in the second configuration. Preferably, the lead engaging member 402 further includes spacers 420 disposed between the ring sections 414. Each of the spacers 420, forms a ring and is disposed around the mandrel 418. A distal spacer 422 may be fixedly attached to a distal end 410 of the mandrel 418 by a suitable fastening means. Or, the distal end 410 of the mandrel 418 may include a raised portion 424 fixedly attached thereto to provide a stop for the elastic members 414. Preferably, the material of the spacers 420 is an incompressible solid, such as rigid plastic, stainless steel, or any other suitable, rigid material.

The eighth embodiment may also include a tubular, elastic jacket 430 disposed over the elastic ring sections 414 and spacers 420 along the entire length of the lead engaging member 404. The elastic jacket 430 is preferably slip fitted over the lead engaging member 404 and attached at each end thereof 432, 434 to the lead engaging member, thus enclosing the elastic ring sections 414 and spacers 420 therein. The distal end 432 of the elastic jacket 430 may be attached to the distal end 410 of the lead engaging member 404 by a band 436 which is fastened about either the raised portion 424 (as shown) or the mandrel 418, or it may be attached to either of each with an adhesive. Similarly, the proximal end of the elastic jacket 430 may be attached to the distal end 473 of the hypotube 472 of the latching mechanism 470 with a band 436, or it may be attached thereto with an adhesive. Alternatively, the distal and proximal ends 432, 434 of the elastic jacket 430 may be similarly attached to the last and first, respectively, distal spacers 438, 428. By enclosing the lead engaging member within the elastic jacket 430, in the unlikely event that a ring section 414 or spacer 420, or a portion thereof, becomes detached from the lead locking device 404, the detached portion will remain contained therein and be prevented from remaining in the patient when the lead locking device is removed. As shown in FIG. 21, the elastic jacket 430 radially expands and longitudinally displaces and/or stretches as the elastic ring sections 414 radially expand under compression in the second configuration, and returns to substantially its original shape when the ring sections are substantially relaxed in the first configuration.

The elastic jacket 430 is preferably made from an elastomeric material, such as polyurethane, or other suitable elastic material. The wall thickness of the elastic jacket 430 may vary depending on the size of the lead locking device.

Preferably, the material of the elastic ring sections 414 is silicon. However, any suitable material is contemplated that sufficiently radially expands upon compression and returns to substantially its original shape when the compressive load is removed. For example, the elastic elements may include a series of beveled elements 440 forming a ring, shown in FIGS. 22 and 23. Each beveled element 440 may be a single element, or, each beveled element 440 may include two symmetric beveled washers 442, 444 disposed in opposing relation to each other. The beveled elements 440 may also have spacers 420 therebetween.

In the eighth embodiment, latching mechanism 470 may be attached to a proximal end of the mandrel 418. The latching mechanism 470 is similar to that described above with respect to the fifth embodiment (FIG. 11), except that the distal end 473 of the hypotube 472 of latching mechanism 470 is not attached to any other member. As shown in FIGS. 20 and 21, when the latching mechanism is positioned such that detent 476 is within indent 478 of attachment portion 474 and a compressive force is applied to the elastic members 414 (and spacers 420) in the second configuration, the distal end 473 of the hypotube 472 buts against a proximal elastic member 428.

Figure 24:
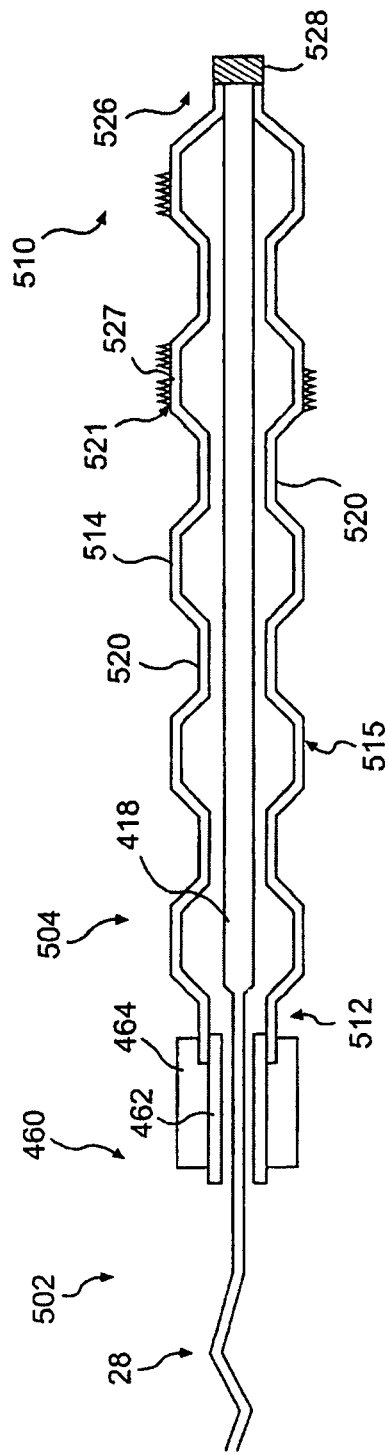
FIG. 24 illustrates a ninth embodiment of the lead locking device of the present invention in a relaxed configuration (first configuration)
Figure 25:
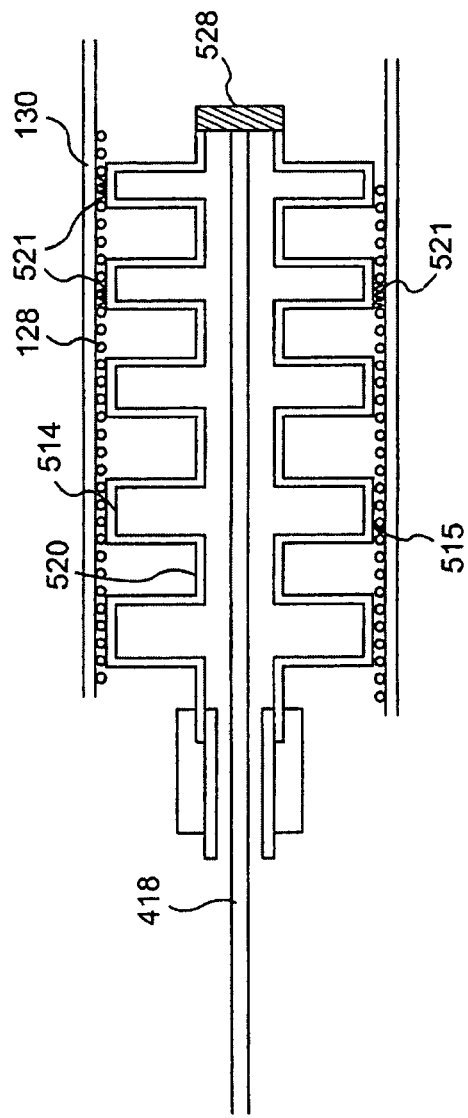
FIG. 25 illustrates the embodiment of FIG. 24 in a deployed configuration (second configuration)

In an alternative ninth embodiment, shown in FIGS. 24 and 25, the series of elastic members of the eight embodiment may include a single expansion element 515, where the single expansion element includes a series of radially expandable elastic sections 514, each section 514 being integrally connected to an adjacent section by reduced diameter portions 520. In this embodiment, the elastic sections 514 are substantially relaxed in the first configuration and radially expanded under a compressive force in the second configuration to engage the lead 130 (FIG. 23). Preferably, the distal end 526 of the single expansion element 515 is fixedly attached to the distal end 510 of the mandrel 418 by a suitable fastening mechanism 528, such as by welding, soldering, gluing, etc. of the single expansion element to the mandrel.

Each section 514 can have various shapes. For example, each section 514 may be a six sided body (FIG. 26), which when compressed, extends radially outward (FIG. 27). Also, although indicated as being axisymmetric in FIGS. 24 and 25, the sections 514 may include extremities at staggered locations 517 about the longitudinal axis 416, as shown in FIG. 28, having four such extremities. To enhance engagement between the each section 514 and lead 130 from within the lumen 128 when in the second configuration, fine protrusions 521 or barbs may be disposed on the outer surface of some, or all, of the sections 514 (FIGS. 28 and 29).

In the eighth and ninth embodiment, the mandrel 418 is preferably coated with TEFLON®, or other similar substance or lubricant to provide reduced friction between the mandrel and elastic sections 420, 440, spacers 420, and the single expandable element 515.

In the ninth embodiment, a press-fit type of latching mechanism 460, similar to the press-fit type latching mechanism 18 of FIG. 2 may be used. An inner and outer hypotube 462, 464 are concentrically arranged to sandwich the proximal end 512 of the single expansion member 515 of the lead engaging member 502 therebetween. In the first configuration, the lead engaging member 502 is stretched so that the inner and outer hypotubes 462, 464 overlaps the crimped section 28 of the mandrel 418, setting the lead engaging member in a stable, stretched configuration (i.e., the first configuration). Alternatively, the latching mechanism 50 (FIG. 4) can also be used.

In both the eighth and ninth embodiments, as with previous embodiments, the lead engaging member engages the lead along at least about 30% of the entire longitudinal length of said lumen of said lead, and preferably substantially the entire length of the lumen of the lead. Preferably, the lead engaging member engages a portion of a proximal end and at least a portion of a distal end of the lumen of the lead.

Also, the lead engaging members 402, 502 have a maximum transverse diameter in the first configuration that is less than substantially all diameters of the lumen 128 of the lead 130 along substantially the entire length of the lead, and the lead engaging members have a transverse diameter in the second configuration that is at least substantially equal to diameters of the lumen of the lead along substantially the entire length of the lead. In the first configuration (relaxed), the elastic members 414, 440, 514 of the lead engaging elements 402, 502 have substantially no compressive load applied thereto. In the second configuration, the elastic members 414, 440, 514 of the lead engaging elements 402, 502 have a compressive force applied thereto so that an outer diameter of each of the elastic members radially expands so that some of the elastic members engage the lumen 128 of the lead 130. Preferably, a majority of the elastic members 414, 440, 514 engage the lumen 128.

In operation, the surgeon inserts the lead locking device 402, 502 into the lumen 128 defined by the lead 130. Then, an axial compressive force is applied to the elastic members 414, 440, 514 of the lead engaging members 404, 504 so that the elastic members of the lead engaging member expand radially outward to engage the lead 130. The surgeon then applies traction to the lead locking device 402, 502, wherein the lead engaging member engages the lead preferably along substantially the entire longitudinal length of the lead.

In the above embodiments, the outer diameters of the lead locking devices may be between 0.013 to 0.032 inches according to current standard leads.

One skilled in the art would recognize from the teachings of the specification that one may provide other configurations which include pliable material or expandable and contractible lead engaging members without departing from the general scope and spirit of the invention. Furthermore, one skilled in the art would recognize from the above teachings that many modifications and variations are possible without departing from the scope and spirit of the invention.

We claim:

1. A method of removing a lead implanted in a patient's body, comprising:
    inserting a lead locking device into a lumen of the lead;
    engaging the lumen of the lead with the lead locking device by increasing the diameter of the lead locking device along at least about 30% of an entire longitudinal length of said lead; and
    applying a traction force to a proximal end of said lead locking device, wherein the traction force is distributed along the engaged portion of the lumen allowing removal of the lead with reduced distortions, disruptions, or breakages of the lead.

2. A method of removing a lead implanted in a patient's body according to claim 1, wherein said at least about 30% of said lumen defined by said lead includes at least a proximal portion and a distal portion of said lumen defined by said lead.

3. A method of removing a lead implanted in a patient's body according to claim 1, wherein said at least about 30% of said lumen defined by said lead includes substantially said entire longitudinal length of said lead.

4. A method of removing a lead implanted in a patient's body according to claim 1, further comprising sliding a catheter over said lead wherein said lead extends along a lumen defined by said catheter.

5. A method of removing a lead implanted in a patient's body according to claim 4, wherein said catheter is a laser catheter.

6. A method of removing a lead implanted in a patient's body according to claim 1, further comprising detaching said lead engaging member from said lead.

7. A method of removing a lead implanted in a patient's body according to claim 6, further comprising re-attaching said lead locking device to said lead.

8. A method of removing a lead implanted in a patient's body according to claim 1, wherein the diameter of the lead locking device is increased along substantially the entire longitudinal length of the lead locking device.

9. A method of removing a lead implanted in a patient's body according to claim 1, wherein the traction force is distributed along a distal portion of the lead and a proximal portion of the lead.

10. A method of removing a lead implanted in a patient's body according to claim 1, wherein the lead locking device concentrically engages the interior walls of the lumen.

11. A method of removing a lead implanted in a patient's body according to claim 1, wherein the lead locking device includes a braided sheath.

12. A method of removing a lead implanted in a patient's body according to claim 11, wherein the braided sheath comprises a plurality of flat wires.

13. A method of removing a lead implanted in a patient's body, comprising:
    inserting a lead locking device into a lumen of the lead;
    engaging the lumen of the lead with the lead locking device along substantially the entire area of at least about 30% of an entire longitudinal length of said lead; and
    applying a traction force to a proximal end of said lead locking device, wherein the traction force is distributed along the engaged portion of the lumen allowing removal of the lead with reduced distortions, disruptions, or breakages of the lead.

* * * * *